United States Patent [19]
Muller et al.

[11] Patent Number: 6,057,421
[45] Date of Patent: May 2, 2000

[54] VARIABLE HEAVY AND LIGHT CHAIN REGIONS OF MURINE MONOCLONAL ANTIBODY 1F7

[75] Inventors: Sybille Muller; Heinz Kohler, both of Lexington, Ky.

[73] Assignee: Immpheron, Inc., Lexington, Ky.

[21] Appl. No.: 08/984,277

[22] Filed: Dec. 3, 1997

Related U.S. Application Data

[63] Continuation-in-part of application No. 08/351,193, Nov. 30, 1994, abandoned.

[51] Int. Cl.[7] ............................. A61K 39/395; C07K 7/04
[52] U.S. Cl. .................. 530/300; 530/387.2; 530/387.7; 530/391.3; 530/388.8; 530/389.7; 424/131.1; 424/138.1; 424/174.1; 424/178.1; 435/327; 514/12
[58] Field of Search .............................. 530/387.2, 387.7, 530/391.3, 388.8, 389.7, 300; 424/131.1, 138.1, 174.1, 178.1; 435/327; 514/12

[56] References Cited

FOREIGN PATENT DOCUMENTS

WO 93/17694   9/1993   WIPO .

OTHER PUBLICATIONS

Herndier et al Hybridoma vol. 12(5), 1993.

Paul, WE Fundamental Immunology Third Edition 242, 1993.

Muller etal, J. Immunology vol. 147 No. 3:933–941, Aug.

Wang et al, Eur J Immunology, vol. 22(7) 1749–1755, 1992.

Weigert et al Nature vol. 276 785–790, 1978.

Rudikoff et al Proc Natl Acad Sci USA vol. 79 p. 1979, 1982.

Panka et al Proc Natl Acad Sci USA vol. 85 3080–3084, May 1988.

Amit et al Science vol. 233 747–753, 1986.

*Primary Examiner*—Julie Burke
*Attorney, Agent, or Firm*—James H. Meadows

[57] ABSTRACT

The amino acid sequences of variable heavy and variable light domains of murine monoclonal antibody 1F7 are reported. Methods of use for products containing these sequences in the diagnosis and the treatment of HIV infection and AIDS are also described.

4 Claims, 23 Drawing Sheets

HIV+

HIV-

1F7 VL

L1
DIVLTNSPASLAVSLGQRATISC<u>KASQSVDYDGDSYM</u>WYQQ

L2
KPGQPPKLLTI<u>AASNLES</u>GIPARFSGSGSGTDFTLNIHPVE

L3
EEDAATYY<u>CQLCNEDPPT</u>FGAGTKQQQK

1F7 VH

H1
QVTLKESGPGILQPSQTLSLTCSFSGFSLS<u>TSFMGVS</u>WIRQ

H2
PSGKGLEWLA<u>HIYWDDDKRYNPSLKS</u>RLTISKDTSSNQDFL

H3
KITSVDTRDTATYYCAR<u>RVSLTAYAMDY</u>WGQGTSVTVSS

VARIABLE HEAVY AND LIGHT CHAIN REGIONS OF MURINE MONOCLONAL ANTIBODY 1F7

REFERENCE TO RELATED APPLICATION

This application is a continuation-in-part of U.S. Ser. No. 08/351,193, filed Nov. 30, 1994, now abandoned.

TECHNICAL FIELD

The present invention relates to the variable domains of a mouse monoclonal antibody 1F7 and their methods of use for the treatment of Human Immunodeficiency Virus (HIV) infection and the symptoms of Acquired Immune Deficiency Syndrome (AIDS).

Antibody 1F7 is produced by a hybridoma cell line deposited on Mar. 8, 1993 with the American Type Tissue Collection, Manassas, Va., and is designated ATCC No. HB 11286.

BACKGROUND

Monoclonal antibodies specific for epitopes of the HIV virus are known. For example, U.S. Pat. No. 4,843,011 to Sarngadharan et al. discloses monoclonal antibodies and hybridoma cell lines for their production that bind particularly to the transmembrane envelope protein gp41, major core antigen p24 and p17 protein of HTLV-III (HIV-1). The patent indicates that the gp41 antibody precipitated a gp160 and a gp41 from cell extracts and demonstrated that gp160 is the primary cellular translational product and gp41 is one of the products of processing during viral maturation.

U.S. Pat. No. 5,120,642 to Schlossman et al. discloses a monoclonal antibody that distinguishes helper inducer and suppressor inducer CD4+ lymphocytes. The monoclonal antibody preferentially binds to the human CD4+ lymphocyte population. The monoclonal antibody detects the 1F7 antigen, which is the 110 kDa glycoprotein surface antigenic determinant of the CD4+ lymphocyte cells.

U.S. Pat. No. 5,166,050 to Shriver et al. discloses monoclonal antibody secreting cell lines specific for envelope glycoprotein gp110 or p25 of the human immunodeficiency virus (HIV).

U.S. Pat. No. 5,169,752 to Ohno et al. discloses production of purified and isolated immunologically active polypeptides, such as antibodies or chimeric antibodies or fragments thereof, which are reactive with the idiotypes of antibodies to human lymphocyte T-4 protein. Claimed is an assay for the detection and quantification of HIV. These products are capable of specific immunobinding with the portion of the HIV virion which is interactive with the T-4 cell surface proteins during infection by HIV. The products neutralize the infectivity of HIV by their reactivity with HIV protein fractions, especially the 60,000 to 80,000 and 65,000 to 67,000 fractions. The assay claimed in this patent detects the protein fraction.

U.S. Pat. No. 5,215,913 to Posner discloses an IgG-1 reactive monoclonal antibody with an HIV-1 antigen. The monoclonal antibody is designated F105. The antibody is capable of blocking the binding of HIV to human cells and preventing infection of human cells by HIV. Also encompassed are anti-idiotypic antibodies against human monoclonal antibody F105.

U.S. Pat. No. 5,217,895 to Ohno et al discloses a purified isolated immunologically active polypeptide in the form of an antibody, chimeric antibody or antibody fragment capable of specific immunobinding with the HIV virion, which is interactive with T4 surface proteins during HIV infection. Molecular weight of the proteins is 65,000 to 67,000.

U.S. Pat. No. 5,245,015 to Fung et al. discloses monoclonal antibodies neutralizing the epitope of the gp120 glycoprotein of HIV.

U.S. Pat. No. 5,275,813 to Yamamoto et al. discloses methods and vaccines against Feline Immunodeficiency Virus (FIV). The vaccine includes wholly and partially inactivated viral cells and cell lines expressing FIV antigens.

U.S. Pat. No. 5,266,478 to Chang et al. discloses monoclonal antibodies which target a neutralization site within the second variable region of human immunodeficiency virus type 1 (HIV-1) gp120. The MAbs define a unique neutralization domain in the V2 region of HIV-1 gp120. They bind to V15P amino acid residues 169–183 of HIV-1 IIIB gp120 and are Ig Gk, k MAbs. The patent discloses other monoclonal antibodies that bind to other sequences of the gp120 protein.

U.S. Pat. No. 5,298,419 to Masuho et al. discloses human monoclonal antibodies which immunologically bind to both gp41 and gp120 envelope glycoproteins of the HIV virus.

Wang and Muller et al., *Eur. J. Immunology* (1992) discloses human monoclonal and polyclonal anti-immunodeficiency virus (HIV-1) antibodies (1F7, IgM, K). It was found that the 1F7 clonotype is shared by human anti-HIV-1 antibodies with different specificities. This publication discloses 1F7 monoclonal antibodies but does not specifically disclose the sequences of the variable light and heavy chain of the monoclonal antibodies or their methods of use.

WO 93/17694 discloses an anti-idiotype antibody which is reactive with more than one type of human anti-HIV antibody. This antibody is 1F7. This publication discloses 1F7 monoclonal antibodies but does not provide any sequence information of the variable light and heavy chain of the monoclonal antibodies or methods of use.

Muller et al., *J. of Immunology*, Aug. 1, 1991, "Generation and specificity of monoclonal anti-idiotypic antibodies against human HIV specific antibodies," discloses the generation of a panel of murine anti-idiotypic antibodies against human polyclonal and monoclonal anti-HIV antibodies. The 1F7 anti-idiotypic antibody is disclosed, which binds to p24 of HIV.

Herndier et al., *Hybridoma*, Oct. 19, 1993, "A non-lymphoma idiotype is indicative and predictive for B cell malignancies in AIDS", discloses that the 1F7 idiotype is expressed on antibodies reactive to different proteins of HIV including gp120, gp41, and reverse transcriptase.

A need exists in the art for additional, improved methods of treating HIV infection, AIDS and/or for delaying the onset of symptoms of the disease. There is also a need for alternative, improved methods for detecting HIV infection, preferably in serum. The amino acid sequences of the variable light and heavy regions of the 1F7 antibody are not known previously. The present invention overcomes the associated deficiencies of previously proposed therapeutic and diagnostic methods.

SUMMARY OF THE INVENTION

The present invention provides specific variable light and variable heavy chains of the 1F7 monoclonal antibody and a method of treating AIDS with monoclonal antibody 1F7 variable light chains, variable heavy chains or functional equivalents thereof. The invention also provides a method for detecting HIV in serum using monoclonal antibody 1F7 variable light chains, variable heavy chains and functional equivalents thereof.

The invention further provides a method of stimulating HIV antigen related and committed B cells to produce broadly reactive and neutralizing antibodies by clonotypic stimulation comprising administering to an infected individual an effective amount of anti-idiotypic antibody 1F7, or compositions comprising the monoclonal antibody 1F7 variable light chains and variable heavy chains or functional equivalents thereof, to elicit an antibody response.

The above and other objects of the invention will become readily apparent to those of skill in the relevant art from the following detailed description and figures. As is readily recognized the invention is capable of modifications within the skill of the relevant art without departing from the spirit and scope of the invention.

DESCRIPTION OF DRAWINGS

FIG. 1 shows supernatants of hybridoma cells were screened for specific binding to H2 and cross-reaction with HIVIG. Two positive clones, 10B3 (IgG2B, K) and 2A11 (IgGK), secreted antibodies that recognized HuMo anti-gp41 Ab (H2) and cross-reacted with HIVIG. The binding of 2A11 to H2 and HIVIG was compared over a wide concentration range. Microtiter plate wells were coated with goat anti-human IgM and IgG, respectively. Different concentrations of H2, HIVIG, normal human IgM, or IgG were added. 2A11 labeled with $^{125}$I was added and binding of concentrations >1 $\mu$g human H2 or HIVIG could be detected.

FIG. 2 shows dose-dependent binding of HIV+ serum antibody to the anti-Id 2A11 was observed. Remarkably, strong binding of total anti-gp120 antibodies to 2A11 was found indicating that 2A11 detects a nonparatopic idiotope present on anti-gp120 antibodies.

FIG. 3 shows Anti-Id (Ab2) binding in pooled human Ig.

FIG. 4 shows Id matching in five individual HIV+ seropositive patient's sera by means of five anti-Id (Ab2).

FIG. 5A shows Id matching of human antibodies in individual sera derived from 20 different HIV+ patients by means of anti-Id antibody 1F7.

FIG. 5B shows mouse anti-Id 1F7 was dotted first on plain nitrocellulose strips and then incubated with dilutions of each of the 20 human HIV+ and HIV− sera. Data presented show a concentration of 2.5 $\mu$g 1F7/dot and a 1/500 dilution of each serum. The two rows on top are composed of 20 dots representing 20 individual HIV+ sera. The two rows on the bottom are composed of 20 dots representing 20 individual HIV− sera. Dark dots represent significant binding of 1F7 to human serum antibodies.

FIG. 5C shows Total IgG in human normal and HIV+ sera. Total IgG concentrations were determined for sera from 20 HIV+ and 20 HIV− normal donors. Each point represents the average of a triplicate (SD<=15% of mean cpm) of serum antibody binding to goat-anti-human IgG derived from either an individual normal blood donor (left side), serum 1 to 20) or from an individual HIV+ patient (right side, serum 21 to 40).

FIG. 6 shows the binding of human HIV+ serum antibodies purified by affinity chromatography on 2A11-coupled Sepharose to HIV-1 Ag. The broken line indicates low binding of normal human IgG to each of the HIV Ag of the HIV Ag panel (cpm<=400).

FIG. 7 shows the binding of human HIV+ serum purified previously by affinity chromatography on 1F7 coupled Sepharose to HIV-1 Ag. The broken line indicates low binding of normal human IgG to each of the HIV Ag of the HIV-1 Ag panel (cpm<=300).

FIG. 8 shows the sequences of the variable light and heavy regions of the 1F7 monoclonal antibody.

FIG. 9 shows the major strategies for intervention at different stages of pathology of HIV infection. The strategies for immune prophylactic and therapeutic intervention to prevent pathogenic deceptive imprinting at different stages of infection with human immunodeficiency virus (HIV) are shown. Stages of prophylactic and therapeutic intervention include (1) using a modified envelope vaccine in which the major gp120 V3-domain epitopes have been masked; (2) using cytokines that can restore a balanced T helper (Th) cell response (Th1>Th2); or (3) using cross reacting anti-clonotypic antibodies to suppress the dominantly responding B- and T-cell clones in order to allow new clones to respond to emerging viral variants, such as the strategy of the present invention. Strategy 3 describes how 1F7 would act on repertoir freeze or failure to control variants.

FIG. 10 shows Western blot analysis. Western blot analysis was performed using commercial HIV-1 Immunblot Kits. Lane 1: binding of HIV-1$^+$ patient #14 serum anti-HIV-1 antibodies to HIV-1 antigen on Bio-Rad nitrocellulose strips, detected by goat anti-human IgG; lane 2: HIV-1$^+$ patient #14 serum's reactivity with 1F7, detected by incubating antigen-captured anti-HIV-1 antibodies with 1F7 supernatants and developing with goat anti-mouse IgM; lane 3: 5 $\mu$g of 1F7-affinity purified serum antibody from patient #14, developed with goat anti-human IgG; lane 4: HIV-1$^+$ patient #3 serum, developed with goat anti-human IgG, lane 5: HIV-1$^+$ patient #3 serum, incubated with 1F7 and developed with goat anti-mouse IgM; lane 6: 5 $\mu$g of 1F7-affinity purified antibody from patient #3, developed by goat anti-human IgG; lane 7: HIV-1$^+$ patient #16 serum, developed with goat anti-human IgG; lane 8: HIV-1$^+$ patient #16 serum, incubated with 1F7 and developed with goat anti-mouse IgM; lane 9: HIV-1$^-$ control serum, developed with goat anti-human IgG; lane 10: HIV-1$^+$ control serum, developed with goat anti-human IgG. All human sera were diluted 1:100.

FIG. 11 shows binding 1F7 Id$^+$ and F6 Id$^+$ antibodies to (11*a*) gp120; (11*b*) p24. Microtiter plates were coated with 200 ng/well of gp120 (IIIB) or p24 and then incubated with human antibodies purified by 1F7 or F6 immunoabsorbents, bound antibodies were detected with goat anti-human IgG. (11*c*) Binding of 1F7 to human antibodies with different specificities. 1F7-coated plates were incubated with human antibodies purified by p24, gp120 (SF2) or PC affinity columns. The antibodies bound to 1F7 were detected with goat anti-human IgG. All human antibodies were purified from #14 HIV-1$^+$ serum.

FIG. 12. SHIV-IIIB infected rhesus monkeys express 1F7-Id on anti-gp120 antibodies. Plasma specimens from normal non-infected rhesus monkeys (control/1 and /2) and SIV infected rhesus monkey (SIV) together with serum from HIV-1 infected human (HIV) are shown in the first four column pairs. The following pairs show ELISA data from the four SHIV-infected rhesus monkeys selected for mAB vaccination. Anti-gp120 (IIIB) antibodies reacting with 1F7 (anti-IIIB/1F7, solid bars) and antibodies binding to rgp120 (IIIB) (anti-IIIB, dashed bars) were detected in independent sandwich. A replicate assay yielded similar results.

FIG. 13. Sera from selected monkeys 441-92, 149-93, 337-91 and 42-93 were analyzed by ELISA for antibodies binding to gp120 IIIB and 1F7 expression. Macaques 441-

91, 149-93, and 331-91 displayed in panel A, B, and C were inoculated with mAb 1F7; macaque 42-93 was inoculated with isotype control mAb TEPC183 (panel D). Pre-vaccination bleeds and sera from the peak response after vaccination are compared for each monkey as described in FIG. 12. Determinations of triplicate ELISA readings are shown as mean and S.D.

FIG. 14. The effect of 1F7 or TEPC183 injections on the neutralization response against HIV-1 IIIB in four macaques. Data are shown in four panels as in FIG. 13. Selected time points (pre-bleed; days after the first mAb inoculation) are represented as serial serum dilutions (X-axis) versus the reduction in the virus-surviving fraction ($V_n/V_0$) on the Y-axis. The vertical bars indicate the standard error of the predicted means from the fitted regression curve (94).

FIG. 15. The effect of 1F7 or TEPC183 injections on the neutralization response against HIV-1 MN in four macaques. Data are shown in four panels as in FIG. 13.

DETAILED DESCRIPTION OF THE INVENTION

Figure 1:
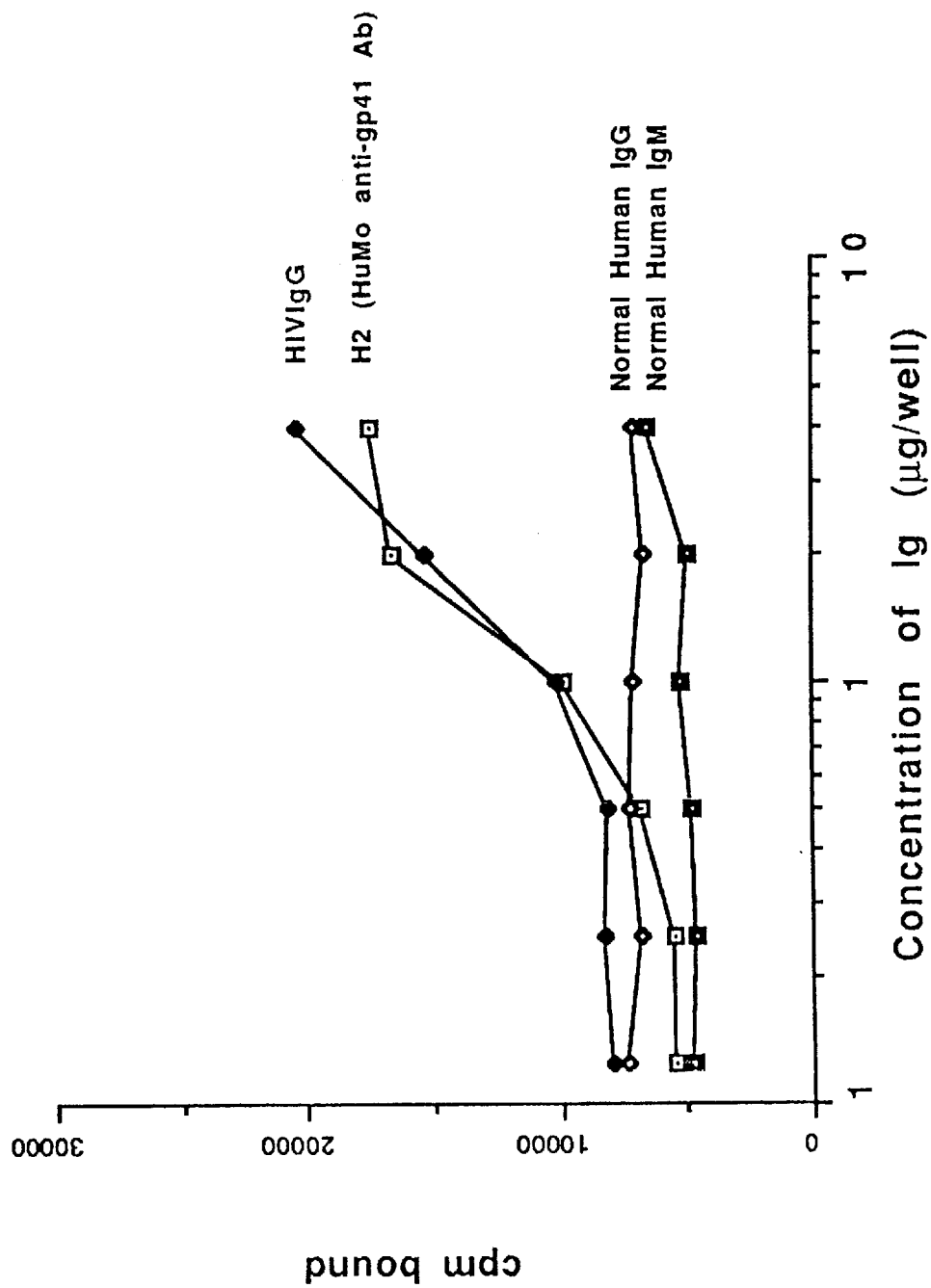

The present invention relates to the determination of the DNA sequences encoding the variable domains of monoclonal antibody 1F7, particularly a mouse monoclonal antibody. The sequences were determined from cloned V genes of heavy and light chains. These genes were cloned using a procedure utilizing specific primers (see Table 1 below) for PCR amplification. The amino terminal sequence from the DNA sequence was confirmed by protein sequence on material produced by gene expressing bacterial clones.

be used to predict the future disease course. In sum, 1F7 has therapeutic, diagnostic and prognostic utilities in the management of AIDS.

Monoclonal anti-idiotypic antibodies against human monoclonal and polyclonal anti-HIV antibodies in seropositive sera were generated. A human anti-gp41 Mab (H2, IgMκ) was used to immunize BALB/c mice and to prepare hybridoma anti-antibodies that react with H2 and not with normal human IgM. Similar monoclonal anti-antibodies were made in BALB/c mice immunized with Ig fraction prepared from a pool of HIV-seropositive sera. Both kinds of anti-idiotypic antibodies reacted with antibodies in pools of seropositive sera and with individual seropositive sera but not with normal human Ig or seronegative sera. The Id-positive Ig from single donors were isolated on two different anti-Id immunoabsorbents and shown to bind to p24 and gp120, respectively.

The detection and isolation of idiotypically cross-reactive human anti-HIV antibodies from seropositive donors demonstrated, for the first time, the existence of shared Id expressed by antibodies against HIV Ag. The utility of cross-reacting anti-idiotypic antibodies as tools to dissect the network regulation of the anti-viral immunity in AIDS was analyzed.

In this application the following abbreviations are used: Id—idiotypic; Ab—antibody; Ig—immunoglobulin; mAb—monoclonal antibody; HIVIG—human anti-HIV Ig: anti-Id—Ab2, anti-idiotypic antibody: Ab1—human monoclonal or polyclonal anti-HIV antibody: Ab1(Id)—human anti-HIV antibody purified on anti-idiotypic antibody coupled to Sepharose: HuMo anti-gp41 Ab- H2, human anti-gp41 mAb: FMDV—foot and mouth disease virus: $HIV^+$—HIV seropositive: $HIV^-$—HIV seronegative: IVIG—human pooled IgG.

TABLE 1

| Primers used in PCR Amplification | |
|---|---|
| <u>1F7 heavy chain:</u> | |
| 5' primer: 5'-ACTAGTCGACATGAAATGCAGCTGGGTCATSTTCTTC | (SEQ ID NO: 1) |
| 3' primer: 5'-CCCAAGCTTACGAGGGGGAAGACATTTGGGAA | (SEQ ID NO: 2) |
| <u>1F7 light chain:</u> | |
| 5' primer: 5'-GGGAATTCATGGAGACAGACACACTCCTGCTAT | (SEQ ID NO: 3) |
| 5' primer: 5'-CCCAAGCTTACTGGATGGTGGGAAGATGGA | (SEQ ID NO: 4) |

The 1F7 antibody sequences and their methods of use are derived from its biological and diagnostic properties in individuals infected with the human immunodeficiency virus HIV-1. 1F7 sequences detect shared idiotopes on antibodies against HIV-1 encoded proteins, such as gp120/160, p24 and reverse transcriptase (RT).

Monoclonal antibody 1F7 expression has been found by the present inventors to be characteristic for the first induced anti-HIV-1 antibody response after infection with HIV-1 virus. Thus, 1F7 is a marker for clones responsive to HIV-1 infection during the initial phase of AIDS disease. Since the response in HIV-1 infection is "locked in" to the initially recruited B cell repertoire and does not change during the chronic and disease phase of HIV-1 infection, 1F7 variable light and heavy regions can be used to suppress the clonal dominance in infected individuals which prevents the response to newly arising viral variants. In addition, 1F7 can enhance the spontaneous apoptosis of T cells from HIV-1 infected individuals. Recognizing this property, 1F7 can be used as a diagnostic tool to describe the severity of T cell abnormalities in an HIV-1 infected individual and may also The long incubation period in HIV infection that precedes the onset of the AIDS disease strongly suggests that the immune response against the virus plays a role in the prolonged disease-free state (1). Better understanding of the factors and mechanisms involved in the humoral anti-HIV immunity provides essential information for the development of immunotherapeutic intervention. In addition, knowledge of regulatory interactions controlling the immunity in HIV-infected patients may provide predictive information on the future disease course.

The present inventors analyzed whether the immune response to HIV is under idiotypic network control as shown or assumed in other immune response against infectious disease, cancer, and autoimmunity (2–11). They analyzed whether Id expressed on antibodies against HIV Ag would produce experimental support for their analysis. However, the analysis of idiotypic network controls in outbred populations is, in a clinically practical sense, only possible if key idiotopes are shared among different individuals.

The existence of shared or recurrent Id in humans has been reported in human autoimmune disease and in other immune responses (10–12). Because some human autoimmune diseases are causatively related to viral infections, it is believed that shared Id also exist in the immune response to HIV infection. Shared Id serve as clinical markers in the disease stage of AIDS and can be used as tools for the prediction of disease progression. It was shown independently by Goldberg et al. (13), Hahn and Ebling (14), and Zanetti (15) that in experimental animal models of autoimmune diseases, idiotypic antibodies can up- and down-regulate the immune response and that the expression of certain idiotopes are correlated with the disease state. The feasibility of using anti-idiotypic mAb to stimulate the production of protective antibodies in sera of mice bearing the corresponding idiotopes has been shown in infection with poliovirus type II (7, 8).

The idea of a functional idiotypic network in HIV-infection has received support by findings that anti-idiotypic antibodies have been used as HIV Ag surrogate for vaccination in rabbits (9).

The role of humoral immunity in AIDS has not been absolutely established; however, there are some disease situations in which neutralizing anti-HIV are protective. For instance, the protective function of maternal anti-HIV directed to the gp120 principal-neutralizing domain in vertical transmission of HIV has been demonstrated recently in infants born to HIV+ mothers (16). Other anti-HIV antibodies are not beneficial because they actually may enhance viral infections (17). It is for this reason that the overall anti-HIV antibodies need to be dissected into beneficial and harmful antibodies. At present, no probes are available to distinguish beneficial and harmful anti-HIV antibodies. If idiotopes are found to be shared by anti-HIV antibodies in a differential manner, such idiotopes could serve as markers to identify anti-HIV antibodies with different biologic function in the disease.

Therefore, the characterization of idiotopes in the humoral anti-HIV response is an important step toward the understanding of the regulation of anti-HIV antibody response and, thus, may be useful in designing better immunotherapies.

In the present application, the generation and specificity of mAb directed against one human mAb and other polyclonal antibodies against anti-HIV envelope, respectively, is described. Each anti-idiotypic antibody is able to detect idiotopes present in human HIV+ sera, but not in normal sera. One monoclonal anti-Id antibody (2A11) was derived from a fusion utilizing spleen B cells from BALB/C mice immunized previously with human anti-gp41 mAb (18). The other anti-Id mAb originated from BALB/c mice immunized with polyclonal HIVIG (19). The finding of cross-reactive or shared idiotopes within a population of seropositive individuals provides the basis for developing a panel of anti-idiotypic antibodies that can be used as specific probes for tracking the Id profile of infected patients.

EXAMPLE 1

Antibodies and Sera

HuMo anti-gp 41 Ab (H2) (IgMκ) with specificity against a conformational loop of the immunodominant region of gp 41 (amino acids 474–758) was purchased from BioInvent, Lund, Sweden (18).

Mouse mAb IM32 (IgGκ) and 11E7 (IgMκ) were obtained from Dr. Pancha Chattopadyhay and C-Y Kang, respectively (20). Polyclonal HIVIG, lot HV102, was obtained from the National Institute of Allergy and Infectious Disease AIDS Research and Reference Reagent Program (ERC Bioservices Corporation, Rockville, Md.). HIVIG contains 98% IgG monomer and 14% fragments and is derived from pooled plasma of 17 HIV+ donors collected in New York, the Netherlands and Paris (19). HIVIG was screened in the laboratory on $NaDoSO_4$/PAGE and Western Blot (Bio-Rad, Richmond, Calif.) before use.

HIV+ plasma specimens were obtained from North American Biological, Miami, Fla. HIV– plasma or serum specimens were available from the American Blood Bank or volunteering laboratory personnel. HIV+ plasma specimens and IgG obtained by affinity chromatography (protein G coupled to Sepharose; Pharmacia Fine Chemicals, Piscataway, N.J.) of plasma specimen were screened by Western Blot on commercial HIV protein containing Nitrocellulose strips (Bio-Rad). Plasma specimens from 20 patients with B cell lymphoma were used. A preparation of human polyclonal anti-gp120 antibodies (total anti-gp120) was obtained. The methods of Kang et al. (21) and N. L. Haigwood and C. J. Scandella, $rgp120_{sf2}$ was used for affinity purification of anti-gp120 antibodies derived from engineered Chinese hamster ovary cells and purified by nonaffinity methods designed to retain the tertiary structure of the protein. Total anti-gp120 antibodies with neutralizing activities were obtained by affinity chromatography purification on $gp120_{osf2-}$ Sepharose of a pool of plasma derived from four HIV+ individuals (21).

IVIG was purchased from Cutter Biological, Elkhart, Ind. IVIG is derived from a large donor pool (>10,000 donors) and issued as a therapeutic drug in humans. The general preparation method is similar to HIVIG preparation (22, 23).

EXAMPLE 2

HIV Ag rgp120 (HTLV-IIIB) was obtained from American Biotechnology, Cambridge, Mass. gp41 consisting of a mixture of linear peptides representing the HIV-1, B-10 immune dominant region (amino acid numbers 588–613) was obtained from International Enzyme Corporation, Fallbrook Calif. rp24 (HTLV-IIIB) was purchased from Pharmacia Genetic Engineering, La Jolla, Calif. P343 was obtained from Dr. Grayson Snyder, State University of New York, Buffalo, N.Y. P343 is a recombinant nonglycosylated envelope protein consisting of the gp120 (HTLV-IIIB) region 343 to 511 of respective amino acid residues expressed by *Escherichia coli*. Y-irradiated HIV-core, i.e., inactivated HIV immunogen that consists of polymerase protein p66, p51, p32 and core p55, p39, p24, p17 and p15 and also transmembrane protein gp41, was obtained from Drs. D. Carlo and F. Jensen, Immune Response Corporation, La Jolla, Calif. (24). RP135 peptides were synthesized at IDEC Pharmaceutical Corporation (La Jolla, Calif.) according to the principal neutralizing determinant of HIV-1 gp120 from HIV-MN and IIIB strains. The rHIVIIIB envelope glycoprotein gp160 was obtained from Dr. Torsten Helting, Pharmacia Genetic Engineering. In order to ensure biologic activity of rHIV reagent, all HIV-1 Ag were tested in ELISA and RIA for binding to standard HIV+ Ig. as HIVIG (9), and to protein, G-purified IgG from plasma of individual HIV+ and HIV– blood donors, respectively.

EXAMPLE 3

Immunization

Six- to eight-wk-old female BALB/c mice were purchased from MTS Laboratories, San Diego, Calif. Different sources of human anti-HIV antibodies were used for immunization of mice to generate anti-idiotypic antibodies: one group of BALB/c mice received initially s.c. one injection of 50 μg of HuMo anti-gp41 Ab in CFA (Sigma Chemical Co., St. Louis, Mo.) followed by two injections of 50 μg HuMo anti-gp41Ab administered s.c. in IFA (Sigma) at days 10 and 20. At day 45 mice were challenged with 50 μg HuMo anti-gp41 Ab i.v. Another group of BALB/c mice received four injections of 50 μg HIVIG in an identical way as described above.

EXAMPLE 4
Purification of Mouse Anti-idiotypic, Polyclonal Serum Antibodies

After each immunization the mice were bled through the retro-orbital sinus and sera were screened for the level of circulating anti-idiotypic antibodies. Sera were at first absorbed on normal human IgM (Sigma) coupled to Sepharose 4B (Pharmacia Fine Chemicals) and then passed over a column consisting of HIVIG covalently coupled to Sepharose.

EXAMPLE 5
Generation and Purification of Mouse Monoclonal, Anti-idiotypic (Anti-anti-HIV) Antibodies Mice injected with HuMo anti-gp41 Ab or HIVIG, which showed a high titer of circulating polyclonal anti-idiotypic antibodies, were killed and spleens removed. The splenic B cells were fused with a nonsecreting mouse myeloma line, SP2/O cells, according to Oi and Herzenberg (25). After 10 days of culture, supernatants were screened by ELISA and RIA. Positive cells were subcloned three to four times and expanded in tissue culture flasks or carried as ascites tumors. mAb derived from supernatant and ascites were precipitated by a saturated solution of ammonium sulfate and further purified by immunoabsorption on protein A-Sepharose (Pharmacia Fine Chemicals) or on goat anti-mouse IgM coupled to Sepharose.

EXAMPLE 6
RIA (1) for Detecting Mouse Anti-idiotypic Antibodies

Microtiter plate wells were coated with 100 μl of carbonate-buffered solution containing 10 μg/ml of human Ig preparations. The coated microtiter well plates were incubated overnight at 4° C. (0.05 M carbonate buffer, pH 9.6) and then blocked with 2% BSS for 2 h at room temperature.

Binding of mouse antibodies (Ab2) to human Ab1 was detected by RIA with the use of goat-anti-mouse Ig (Fisher Biotech., Pittsburgh, Pa.) labeled with $^{125}$I (ICN Biochemicals, Irvine, Calif.). A total of 100,000 cpm/well of $^{125}$I-labeled goat anti-mouse Ig (total Ig or an IgG/IgM mixture) was added to each well and incubated at 37° C. for 1.5 h. The plates were washed with PBS and cpm bound were counted in a gamma scintillation counter (Nuclear-Medical Laboratories, Dallas, Tex.). IgM, IgG, IgO or a mixture of IgM/IgG (1/1) were detected by using parallel wells. In a modified "capture" RIA microtiter plate wells were coated with HIV-1 gp120 (American Biotechnology, Cambridge, Mass.) or gp41 peptide (Enzyme International Corp.), before adding HIVIG. Hybridoma antibodies that bound to human antibodies specific for HIV envelope and not to normal human Ig were selected as potential anti-idiotypic antibodies (Ab2). HIVIG was also captured by HIV-1 core protein Ag (rp24; Pharmacia Genetic Engineering) and HIV-1 core (Immune Response Corporation, La Jolla, Calif.) to detect Ab2 binding to human anti-HIV core protein antibodies.

In another RIA, microtiter plate wells were coated with 100 μl of 10 μl/ml of goat anti-human IgM or IgG for detection for h2 or HIVIG binding of Ab2. Varying amounts of normal human IgM or IgG as well as HuMo anti-gp41-IgM (H2) and HIVIG, respectively, were added. A total of $2 \times 10^5$ cpm of $^{125}$I-labeled anti-Id was added and its binding to idiotopes on H2 and HIVIG was determined by measuring cpm of bound antibody.

EXAMPLE 7
RIA (2) for Detecting Human Antibodies Binding to Murine Anti-id

Affinity chromatography-purified Ab2 were used for detection of Id-carrying human polyclonal serum antibodies. Microtiter plate wells were coated with 1 μg/well of each purified mouse monoclonal anti-idiotypic antibody (Ab2) (100 μl of 10 μg/ml). Plate wells were blocked with 2% BSA and incubated for 2 h at room temperature. After repeated washes with PBS, 100 μl of serial dilutions of plasma specimens derived from HIV+ and normal healthy blood donors, respectively, were added. A total of 100,000 cpm/well of $^{125}$I-labeled goat anti-human IgG was added.

Purification and Characterization of Human Ab1 on Ab2-Sepharose

Two individual plasma specimens containing a high titer of HIV-1 core (p55, p17, p24) as determined by Western blot with the use of commercial nitrocellulose strips (Bio-Rad) were purified according to Garmendia et al. (26) by affinity chromatography with anti-Id 2A11 or 1F7 coupled to Sepharose-4B. The conjugation of anti-idiotypic antibodies to Sepharose was performed by using standard protocols (27, 28).

After absorption and elution of the plasma specimens containing Ab1 on anti-Id-Sepharose columns, the Ab1 enriched for binding to each anti-Id (Ab1 (Id)) were tested for specificity to a panel of HIV-1 Ag by RIA.

Microtiter plate wells were coated with HIV-1 Ag as described previously (RIA 1). Then 100 μl of Ab1 (anti-Id) in concentrations from 100 ng to 10 μg/ml and after incubation and washing. $10^5$ cpm/well of $^{125}$I-labeled goat anti-human IgG, were added.

Iodination of Human Polyclonal and Mouse Anti-id-mAb

Human IgG and mouse mAb purified by affinity chromatography were iodinated for use as labeled reagents in RIA and immunoblotting according to the chloramine T method as described (29).

EXAMPLE 8
ELISA for Detection of Mouse Anti-idiotypic Antibodies

A modification of the ELISA procedure of Engvall and Perlman (30) was used. Microtiter plate flat bottom wells were coated in standard ELISA with 10 ng/well HuMo anti-gp4 antibodies, HIVIG (100 nl of 200 ng/ml in carbonate buffer), 20 ng/well of normal human polyclonal IgM and IgG, respectively (100 μl of 200 ng/ml in carbonate bugger). Serial dilutions of individual (or pooled) sera of mice or culture supernatant from hybridomas generating anti-idiotypic antibodies were added. Mouse anti-Id bound were detected with enzyme-linked goat anti-mouse Ig. After 1 h of incubation at room temperature, the trays were washed with PBS. Next, 0.02 ml of culture supernatant of serial and diluted sera of different amounts of antibody (range of 0.5 to 10 μg/ml) in 0.08 ml of 1% BSA-PBS containing 0.5% Tween and 20 were added to the wells. The tray was incubated overnight at 4° C., washed with PBS, and 0.1 ml of the enzyme-labeled antibody, diluted at $\frac{1}{1000}$ in 1% BSA-PBS containing 0.5% Tween 20 was added. After incubation for 4 h at room temperature, the plate was washed and developed with 0.1 ml of phosphatase substrate (Sigma) solution in diethanolamine buffer at pH 9.6 (30 mg substrate/50 ml buffer). The absorbance was measured on an Artek ELISA Reader at 405 nm (Artek Systems Corporation, Farmingdale, N.Y.).

EXAMPLE 9
ELISA for Detection of Human Antibodies (Ab1 (Id))

In order to detect Id-carrying polyclonal antibodies (Ab1 (Id)) derived from HIV+ individuals, a modified "sandwich" ELISA was used. Briefly, 96-well flat bottom plate wells were coated with 100 µl of a carbonate-buffered solution containing 5 µg/ml of the mouse anti-Id and blocked with 2% BSA. Aliquots (100 µl) of each sample containing human sera diluted 1/100 in 1% mouse serum in PBS were added to the plates in triplicate. Next, 100 µl of the 1% goat serum solution containing 1 µl/ml of biotin-labeled mouse anti-Id was added, followed by 50 µl of an avidin-horseradish peroxidase conjugate (TAGO, Burlingame, Calif.). The assay was revealed with 2.2-azino-bis (3-ethylbenz-thiazoline-G-sulfonic acid) (Sigma) with OD determined at 405 nm. All incubations were for 1 h at 37° C.; plates were washed five times with PBS between all steps.

Biotinylation of antibodies was done by using the N-hydroxysuccinimide ester of biotin (Sigma). Biotinylation with succinimide ester was performed according to Bayer and Wilchek (31).

EXAMPLE 10
Immunoblotting for Detection of Human Polyclonal Serum Antibody Recognition by Anti-Id Binding of the mouse anti-idiotypic mAb (Ab2) to various human polyclonal antibodies in HIV+ donors and from healthy control donors was demonstrated. For this, we developed a modified immunoblotting method; strips of nitrocellulose sheets (Bio-Rad) were at first dot-blotted with 10 µl of various concentrations of mouse monoclonal anti-Id (range 0.5 to 10 µl/ml). The strips were then washed 5 min with 0.05 M Tris-HCl buffer (pH 7.4) containing 0.2 M NaCl and 0.1% Tween 20. Nonspecific binding of antibodies (Ab1) to sheets was reduced by a blocking buffer containing 10% horse serum +0.5% Tween 20 in 0.05 M Tris-HCI (pH 7.4)+0.2 M NaCl for 1 h at room temperature. Each strip was then placed in a single tray and 10 ml of HIV+ or HIV− donor sera diluted 1/500 in the blocking buffer were added and incubated for 3 h. After this, each strip was washed thoroughly with buffer and again blocked as described above for 30 min at room temperature. Then $^{125}$I-labeled goat anti-human IgG ($10^6$ cpm/ml) in blocking buffer was added and incubated for 3 h at room temperature. After incubation, the strips were extensively washed, dried, and exposed to Kodak XAR-5 film (Eastman Kodak Co., Rochester, N.Y.) at −70° C. for at least 3 h and then developed.

EXAMPLE 11
Polyclonal Mouse Anti-idiotypic Antibodies Detect Id Shared by a Human Monoclonal Anti -gp41 Ab (H2) and Human Polyclonal Anti-HIV Antibodies (HIVIG)

Human monoclonal and polyclonal antibodies directed against HIV envelope glycoprotein epitopes were used to generate mouse anti-idiotypic mAb with the purpose of using them to screen for Id expression of anti-HIV antibodies. As such, human antibodies (Ab1 ) served as Ag to produce a second anti-idiotypic antibody (Ab2) directed against Id on Ab1 in mice.

BALB/c mice were immunized four times s.c. and challenged one time i.v. with HuMo anti-gp41/HIV antibodies. The mouse sera were assayed for the presence of polyclonal antibodies specifically binding to H2 HuMo anti-gp41/HIV antibody (IgM). Polyclonal anti-anti-gp4/HIV antibodies could be detected in all 12 BALB/c mice immunized with HuMo H2. Anti-isotypic antibodies were removed by absorbing the pooled mouse sera on human, polyclonal IgM coupled to Sepharose. These anti-anti gp41/HIV antibodies were further purified by affinity chromatography with the use of pooled HIVIG coupled to Sepharose as immunoabsorbent. The binding of polyclonal anti-idiotypic antibodies to HuMo anti-gp41 Ab (H2) could be reduced when absorbed on HIVIG-Sepharose. Antibodies binding to H2 could be eluted from HIVIG-Sepharose (date not shown).

The cross-reaction of polyclonal mouse anti-Id directed to human gp41/HIV mAb (H2) with HIVIG indicates that HuMo anti-gp41 Ab share idiotopes with antibodies present in this pool of human HIVIG. Therefore, mouse monoclonal anti-Id directed to H2 were generated and screened for cross-reactivity with HIVIG.

EXAMPLE 12
Mouse Anti-Id mAb Recognizes Common Idiotopes on Human Monoclonal-anti-gp41 Ab and Heterologous Human Polyclonal Anti-HIV Antibodies Two BALB/c mice previously immunized with H2 that showed the highest titer of polyclonal anti-idiotypic, anti-H2-antibodies were sacrificed and their B cells were fused with SP2/O cells and cloned under limited dilution conditions. Supernatants of hybridoma cells were screened for specific binding to H2 and cross-reaction with HIVIG. Two positive clones, 10B3 (IgG2B, K) and 2A11 (IgGK), secreted antibodies that recognized HuMo anti-gp41 Ab (H2) and cross-reacted with HIVIG. The binding of 2A11 to H2 and HIVIG was compared over a wide concentration range. Microtiter plate wells were coated with goat anti-human IgM and IgG, respectively. Different concentrations of H2, HIVIG, normal human IgM, or IgG were added. 2A11 labeled with $^{125}$I was added and binding of concentrations >1 µg human H2 or HIVIG could be detected (FIG. 1).

Figure 2:
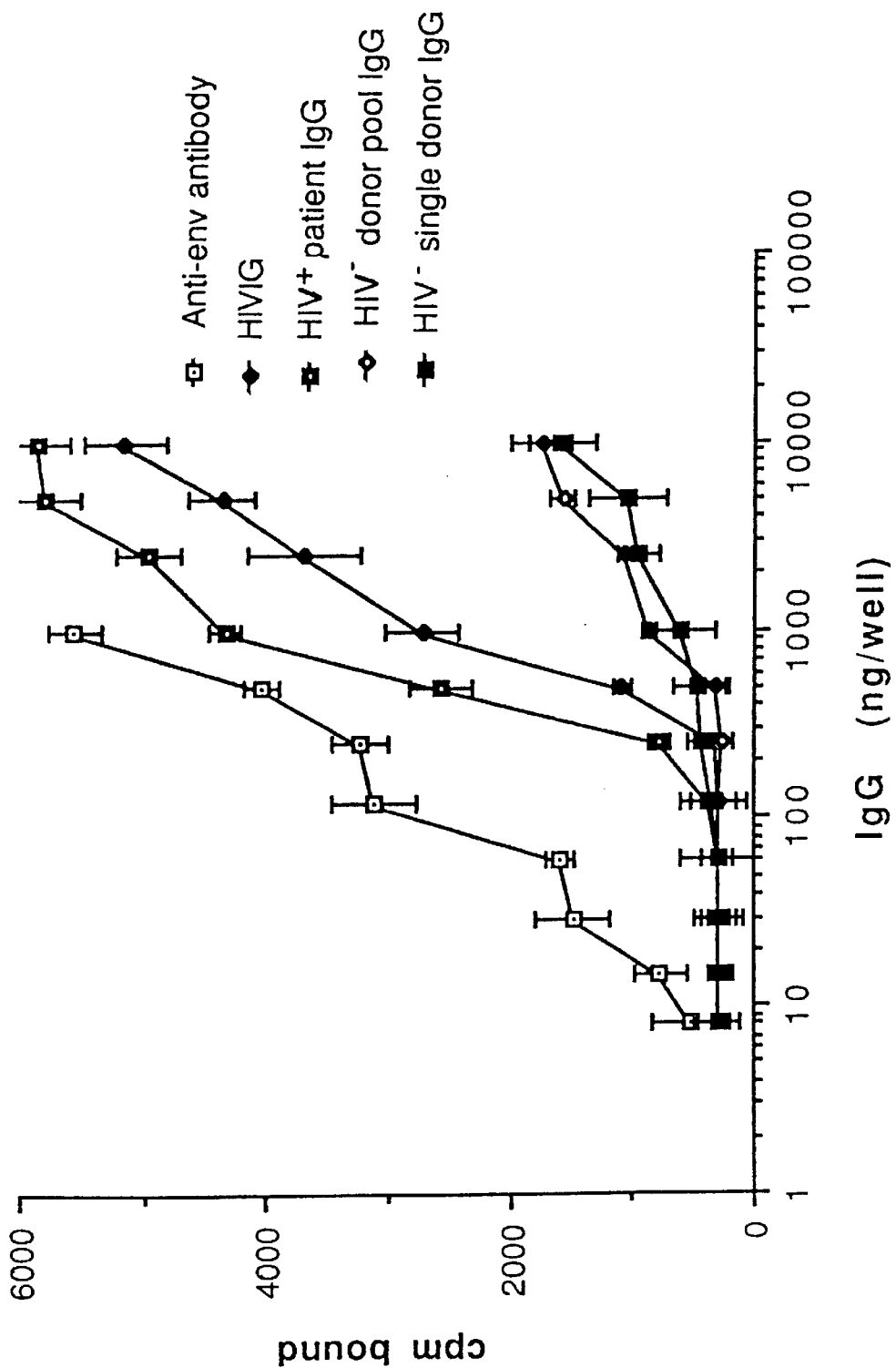
Figure 3:
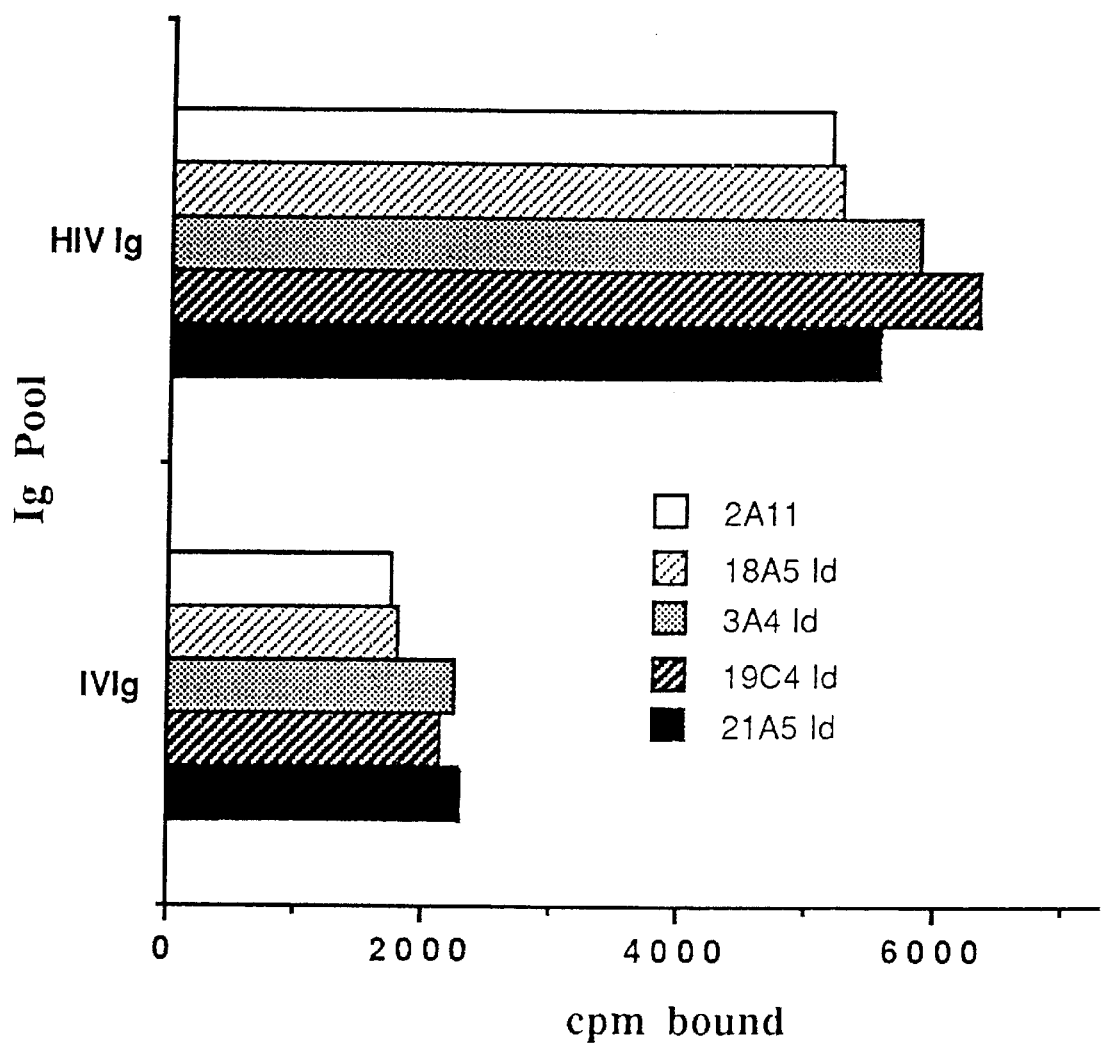
Figure 4:
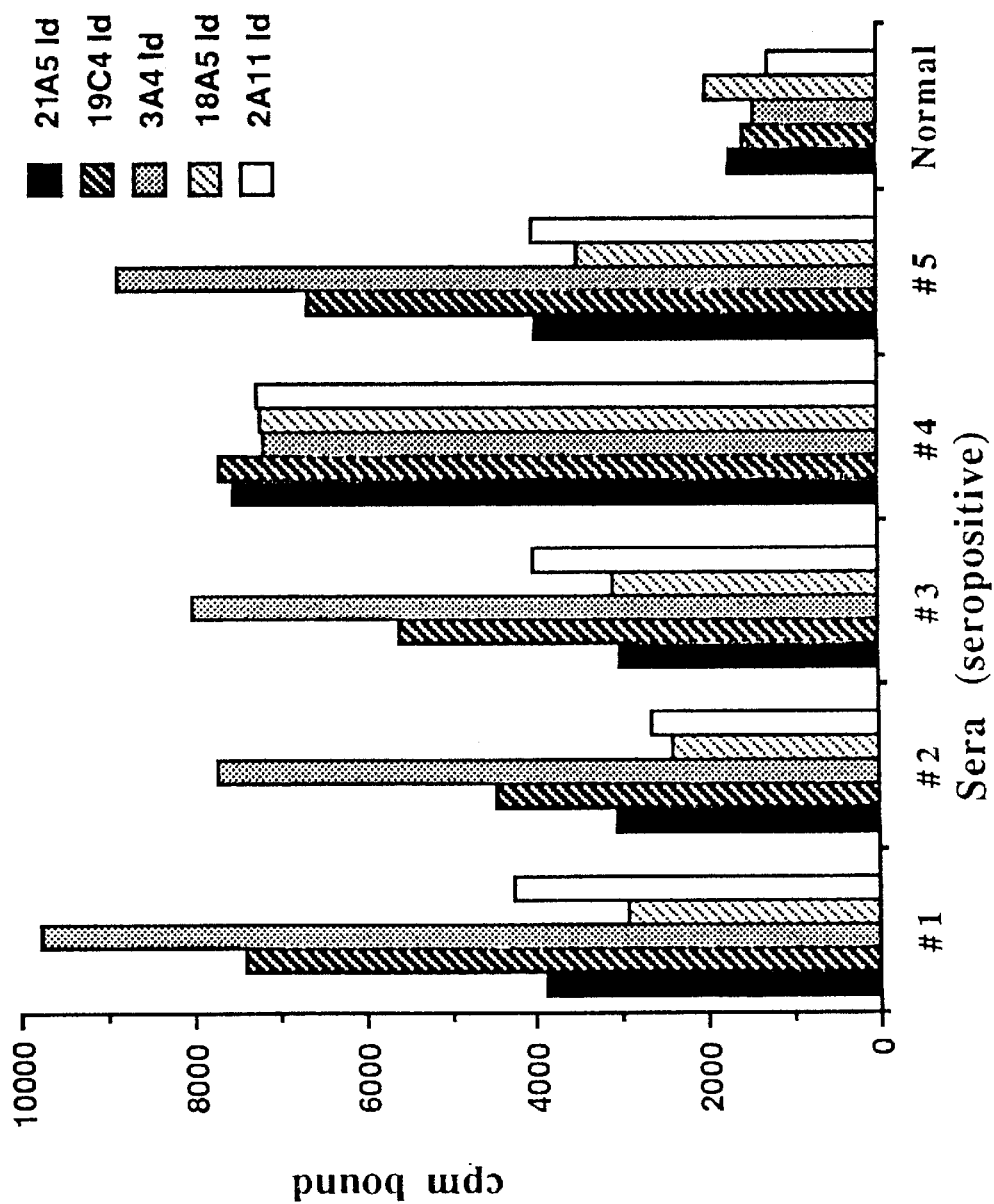

In an experiment in which suppression of 2A11 binding to H2 by cross-reacting HIVIg and HIV+ serum was studied, no competitive inhibition of 2A11 binding to H2 by polyclonal HIV+ Ig was found. This indicates that the cross-reactivity of 2A11 with polyclonal HIV+ Ig is not overlapping with the paratopic, i.e., H2-binding site of 2A11. However, the cross-reaction of the H2-specific anti-Id 2A11 to HIVIg was confirmed in a different RIA in which protein A chromatography-purified unlabeled 2A11 was used to coat microtiter well plates. Different concentrations of HIVIG, protein Ga affinity chromatography purified IgG derived from an individual HIV+ or HIV− donor, and IgG from pooled normal plasma (IVIG) were added to 2A11-coated wells. Also, binding of affinity-purified total anti-gp120 antibodies to 2A11 was determined. Dose-dependent binding of pooled and individual HIV+ IgG to anti-Id 2A11 was revealed with $^{125}$I-labeled goat anti-human IgG. As seen in FIG. 2, dose-dependent binding of HIV+ serum antibody to the anti-Id 2A11 was observed. Remarkably, strong binding of total anti-gp120 antibodies to 2A11 was found indicating that 2A11 detects a nonparatopic idiotope present on anti-gp120 antibodies.

The 2A11-reactive site on H2 and the 2A11-reactive sites on serum anti-gp120 antibodies appear to be unrelated except that both can interact with 2A11. The inability of the HIVIG binding to linear peptides of gp41 and HIVIG binding whole envelope glycoprotein gp160 preparation to inhibit the binding of 2A11 to HIVIG supports this interpretation.

EXAMPLE 13
Generation of a Mouse-anti-Id mAb Panel for Detection of Idiotopes Shared by Heterologous Human Polyclonal Anti-HIV Antibodies Subsequently, additional mouse anti-idiotypic mAb in BALB/c mice immunized with pooled human polyclonal HIVIG were generated. Anti-Id Ab2 clones (18A5, 3A4, 19C4, 21A5, 1F7, and 6E8) were selected from a large number (>100) of hybridomas by screening hybridoma supernatants for specific binding to HIVIG captured on the plate by HIV proteins. The Ab2 hybridomas were supercloned three times and maintained in culture longer than 3 mo. Four Ab2 (i.e. 18A5, 3A4, 19C4, 21A5) were binding to HIVIG captured by HIV envelope glycoproteins, and two Ab2 (i.e., 1F7 and 6E8) were binding preferentially to HIVIG captured by HIV-1 core proteins. Non-HIV-related mouse mAb 1M32 and 11E7 did not bind to HIV-captured human IgG or normal human Ig (data not shown). When HIVIG was captured by commercial nitrocellulose strips containing HIV Ag (Bio-Rad strips) 1F7 and 6E8 bound exclusively to HIVIg captured by p24.

EXAMPLE 14
Id Screening of Seropositive and Negative Sera

In the preceding section the generation and specificity of monoclonal anti-Id raised against pooled polyclonal sera from seropositive individuals and against a human anti-gp41 mAb was described. The reactivity of purified Ab2 with Ig from seropositive and normal individuals was obtained. The binding of five purified Ab2 to Ig fractions from pools of normal and infected donors was determined. All five Ab2 demonstrated significantly higher binding to HIVIG over binding to IVIG pool. These results confirm the above described specificity of the Ab2.

The reactivity of the five Ab2 with individual sera from HIV-infected individuals was determined. All five sera had higher binding to Ab2 than to a representative normal donor; however, the seropositive sera showed different patterns of Ab2 binding. For example, in serum 4, the reactivity of all five Ab2 was equal, whereas the other four sera showed a different pattern of Ab2 binding. These results indicate a variability in the Ab2 reactivities with different seropositive sera.

To further pursue the finding of Ab2 variability among individual seropositive sera, 20 sera from HIV-infected donors were compared with 20 normal sera. In addition, 1F7 Id screening was performed with sera of 3 patients with SLE and 20 patients with B cell lymphoma as non-HIV-related diseases. 1F7 was selected for Ab2 recognition of serum antibody in a population of different blood donors because it appeared to be the antibody with the highest affinity binding to HIVIG in ELISA and Western blot in comparison to the other Ab2. Purified 1F7 Ab2 was coated onto plastic wells and 1/100 diluted human sera was added and incubated overnight. Biotin-labeled 1F7 added together with enzyme conjugated avidin was used to develop ELISA color. The general reactivity pattern with normal sera and sera with non-HIV-related diseases was lower than with seropositive sera. Some seropositive sera had significantly higher reactivity than normal and infected sera, whereas other seropositive sera fell within the normal range. This finding demonstrates that an Ab2 against a pool of polyclonal Ig from infected donors selectively reacts with individual sera from infected donors. These results were confirmed by using a dot-blot method in which 1F7 was dotted on plaint nitrocellulose strips and then incubated with 1/500 diluted individual HIV+ and HIV− human sera, respectively (see FIG. 5B). A similar distribution of Id expression of serum antibodies was observed, i.e., more than one-third of HIV+ sera reacted with 1F7, whereas HIV− sera did not show comparable binding to 1F7.

Figure 5A:
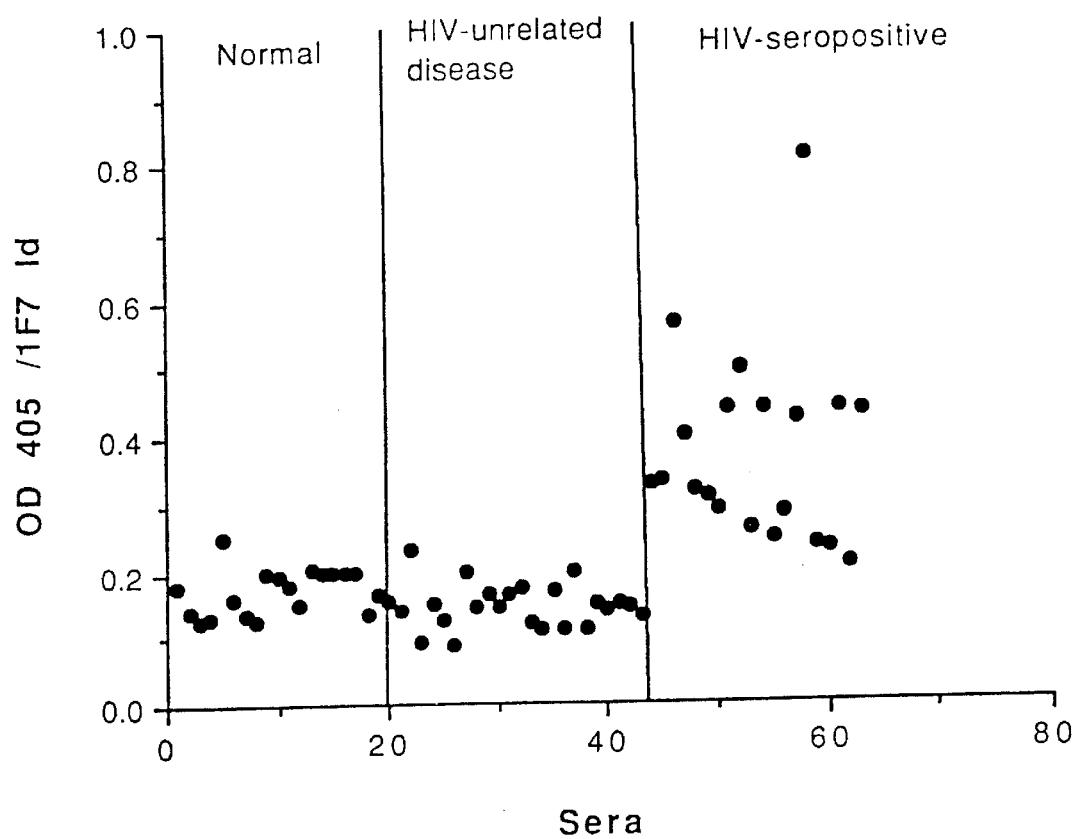
Figure 5B:
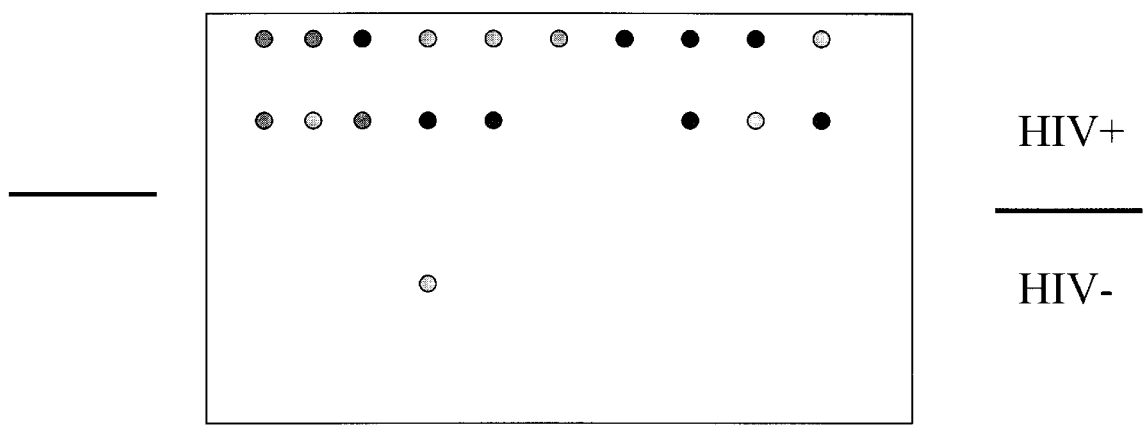
Figure 10:
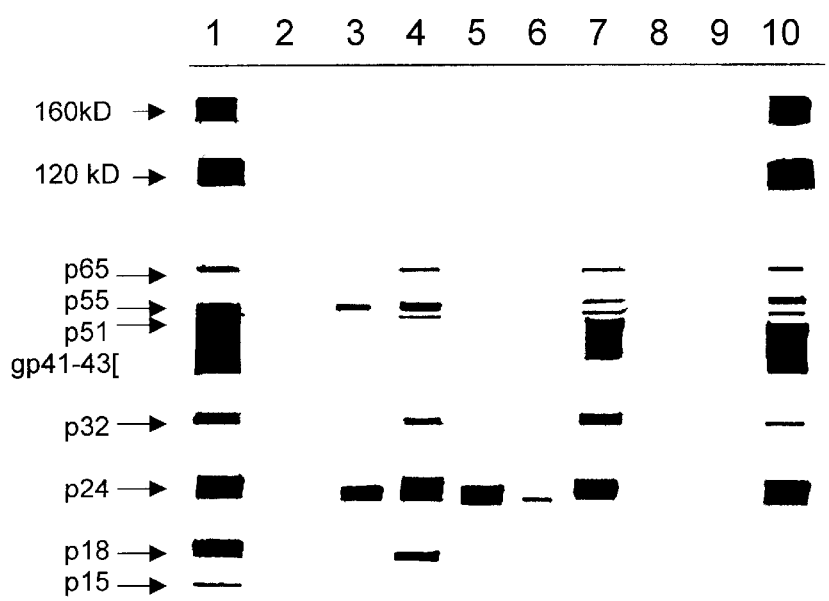
Figure 5C:
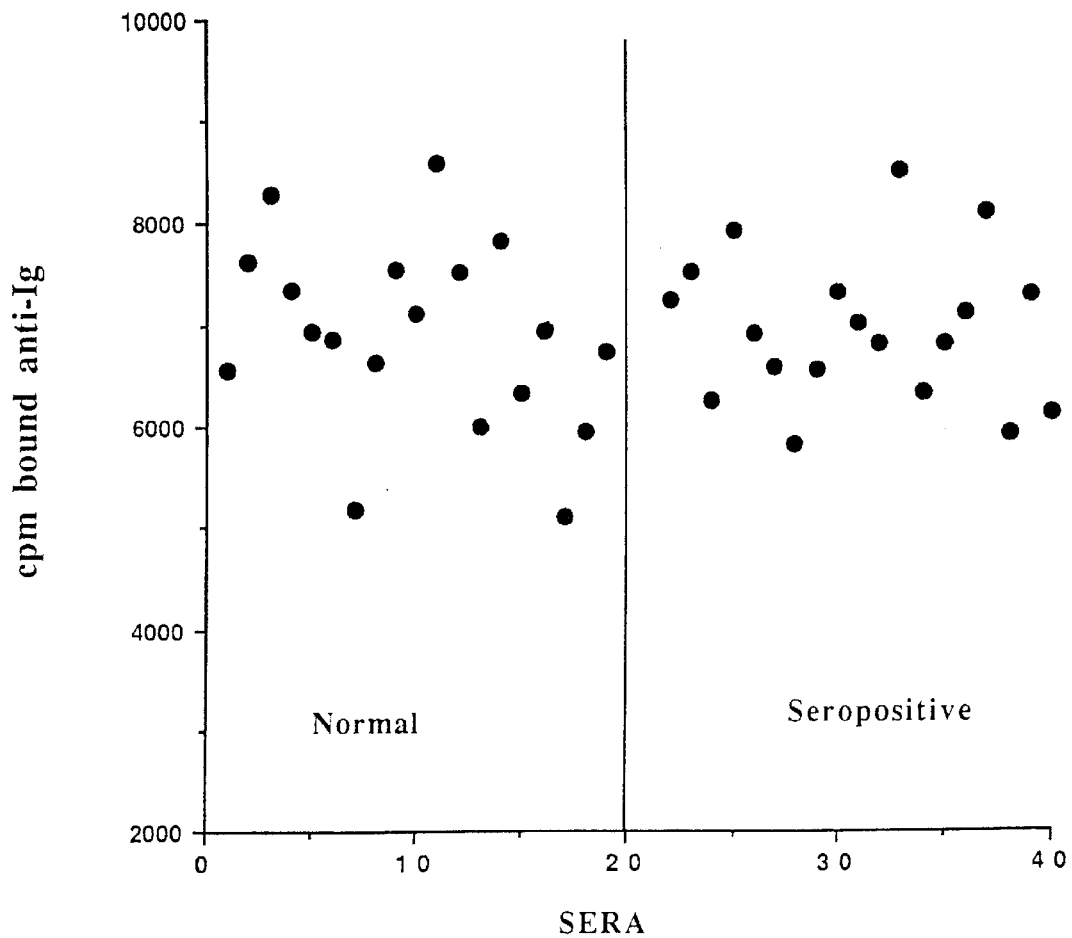
Figure 6:
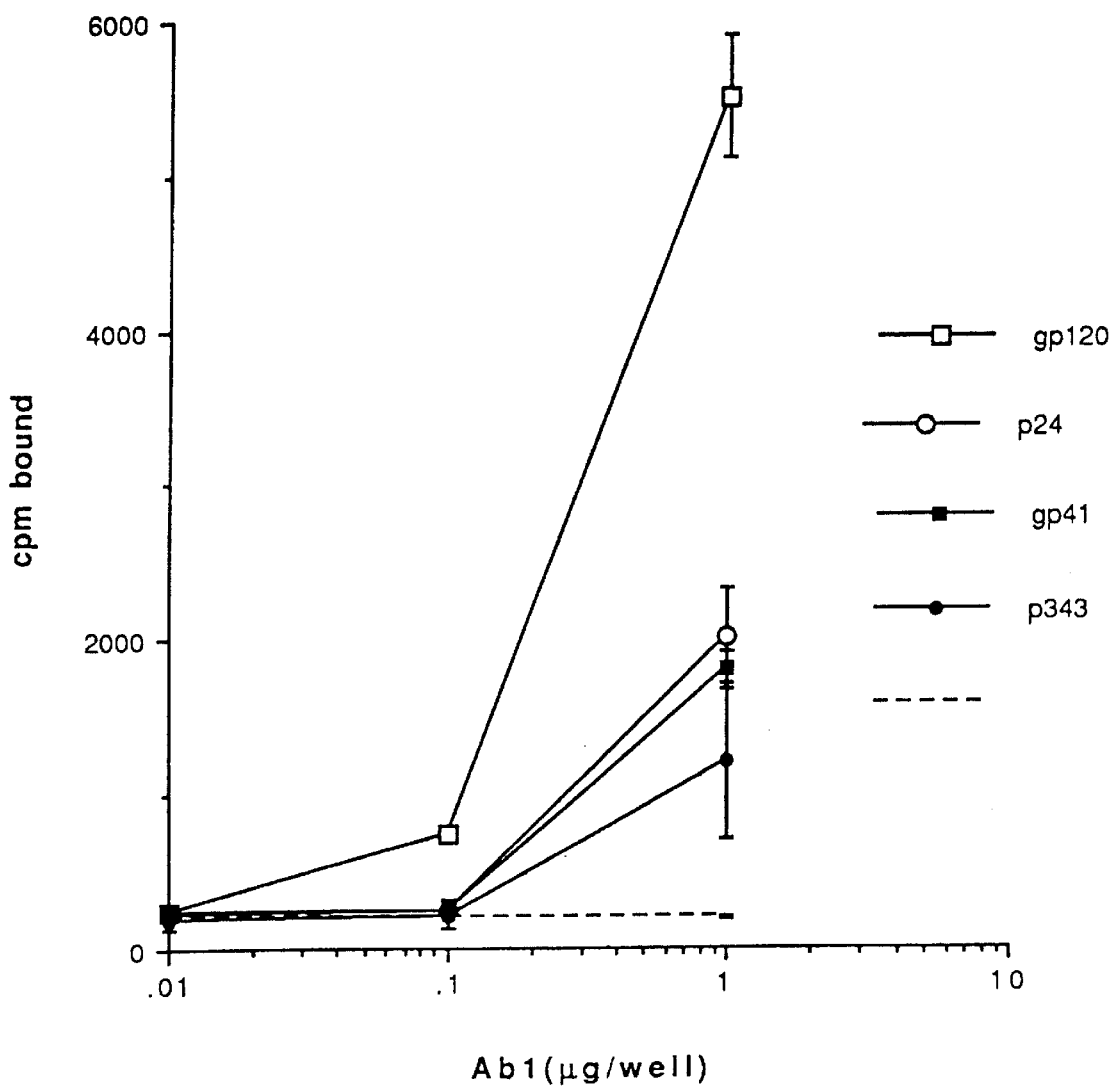
Figure 7:
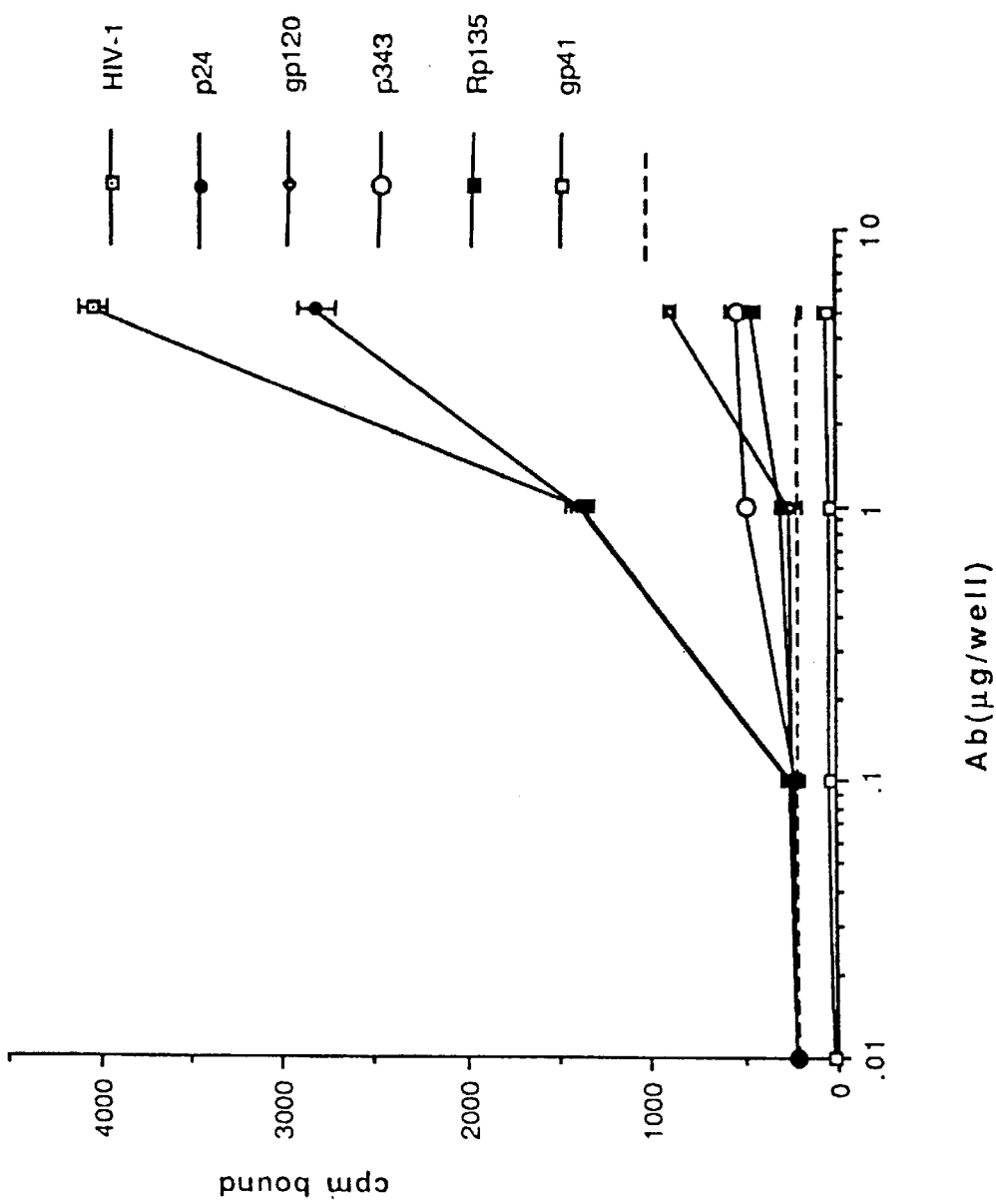

The reactivity of Ab2 with seropositive sera could result from a general increase in Ig levels, which is often observed in certain stages of the AIDS disease (32). Thus, total Ig in the panel of 20 seropositive was measured and normal seronegative sera used in the 1F7 Id binding assay. FIG. 5C shows the Ig detected by an ELISA with the use of a polyvalent anti-human Ig antiserum. No significant differences are seen in the amount of detected Ig between the normal and seropositive panel. Thus, the selective increase of Ab2 reactivity in some seropositive donors is not caused by a general polyclonal Ig increase.

EXAMPLE 15
Characterization of Id-positive Antibodies

It was shown that in certain seropositive sera, Id are found to be increased over levels detected in normal sera. This increased Ab2 reactivity, however, does not indicate the Ag specificity of the Id-positive Ig. To address the question of epitope specificity of Id+ Ig the Ig on an anti-Id immunoabsorbent was purified. Whole plasma from one seropositive individual reactive with a panel of HIV-Ag gp120, p343, p24, gp41 and who typed positive in the Ab2 screen with 2A11 Ab2 was applied to a 2A11 Sepharose column. The acid eluted material was assayed by RIA for binding to a panel of HIV-1 Ag. The 2A11-eluted material binds to insolubilized gp120 preferentially indicating that the 2A11-positive Ig (Ab1 (2A11)) contains gp120-specific antibody. Ab1 (2A11) does not bind to gp41 peptide, a linear peptide presenting amino acids from the B-10 immune dominant region (amino acid numbers 588–613). 2A11 is directed against H2. H2 recognizes a conformational loop of gp41 and does not bind to gp41 Ag blotted on Bio-Rad nitrocellulose strips. Therefore, the anti-H2 antibody 2A11 reacts only with human serum antibodies that are directed to sites of the native, three-dimensional gp41.

However, what was unexpected was the binding of Ab1 (2A11) to gp120 because 2A11 was raised against a human anti-gp41 mAb. This finding indicates that 2A11 recognizes an idiotope coexpressed by anti-gp41 and anti-gp120 human antibodies. The sharing of idiotopes between antibodies with different epitope specificity has been recently recognized as so-called regulatory idiotope (12, 13). The negative binding of 2A11 Id to the recombinant 343 fragment further defines the epitope specificity of the 2A11 Id+ antibody, assigning it to the C-terminal portion of gp120 not past position 343.

Microtiter plates were coated with p24, gp120 (IIB or SF2, RT and tetanus toxoid (all 200 ng/well) then blocked with 2% BSA, HIV-1+ sera diluted 1:100 with PBS were added and incubated for 2 h. After washing, the plates were incubated with 1:5000 diluted peroxidase-conjugated goat anti-human IgG for 1.5 h. Bound antibodies were visualized using OPD at 490 nm. The ELISA for 1F7 was similar to that above, however, after washing, the plates were incubated with 1:2000 diluted peroxidase-conjugated goat anti-human IgM for 1.5 h. Results appear in Table 2.

TABLE 2

Co-expression of 1F7 Id on anti-HIV-1 antibodies in 40 HIV-1+ sera.

| Antibody | No. positive sera | 1F7 Id+ | Percent 1F7 Id+ |
| --- | --- | --- | --- |
| Total anti-p24 | 30 | 18 | 60 |
| Total anti-gp120 | 36 | 16 | 44.4 |
| Total anti-RT | 15 | 12 | 80 |
| Total anti-tetanus toxoid | 39 | 0 | 0 |
| Anti-p24 + anti-gp120 + anti-RT | | 0 | 22.5 |
| Anti-p24 + anti-gp120 | | 1 | 2.5 |
| Anti-gp120 + anti-RT | | 1 | 2.5 |

TABLE 2-continued

Co-expression of 1F7 Id on anti-HIV-1 antibodies in 40 HIV-1+ sera.

| Antibody | No. positive sera | 1F7 Id+ | Percent 1F7 Id+ |
|---|---|---|---|
| Anti-p24 + anti-RT | | 1 | 2.5 |
| Anti-p24 or anti-gp120 or anti-RT | | 11 | 27.5 |
| Total | | 23 | 57.5 |

1F7 Id expression was tested with ELISA (see Table 3 below). Microtiter plates were coated with 1F7 (500 ng/well) overnight, then blocked with 2% BSA. HIV-1+ human sera diluted 1:100 with PBS were added to plates, and incubated 2 h. After five washes with PBS, the plates were incubated with a 1:5000 dilution of peroxidase-conjugated goat anti-human IgG for 1.5 h and developed with OPD. HIV-1− human sera (109) were tested with same ELISA for establishing the cutoff value. HIV-1− human sera consisted of 3 serum samples from systemic lupus erythematosus, 27 sera from B cell lymphoma or leukemia and 79 normal human sera from blood bank. The mean +2SD (0.047+2×0.037=0.121) of $A_{490}$ in HIV-1− sera was considered as cutoff value. The HIV-1+ sera were considered 1F7 Id+ if $A_{490}$ was above 0.121.

Id binding on 1F7 immunoabsorbent column was purified from seropositive, 1F7 reactive serum. 1F7-eluted Ig preferentially binds strongly to rp24 and also to a HIV-1 core preparation devoid of gp120 (33). Thus, the 1F7 Id appears to be primarily associated with an anti-core antibody. As control determined in ELISA, 2A11 and 1F7 did not bind to total anti-phosphorylcholine antibodies (34) derived from normal human plasma affinity purified on a phosphorylcholine column.

TABLE 3

1F7 Id expression in HIV-1+ sera from American and European individuals.

| | American | European | Total |
|---|---|---|---|
| No. tested[a)] | 204 | 125 | 329 |
| LF7 Id+ (%) | 155 (76.0) | 84 (67.2) | 239 (72.6) |

The inventors determined whether idiotopes in sera from infected individuals can be identified that are preferentially expressed on antibodies against HIV-1 Ag. This question arises because Id matching may provide precise information on the determination of biologically effective, neutralizing anti-HIV antibody levels. Finding idiotopes associated with disease-specific antibodies might make them useful as markers for predicting disease progression as well as for disease management and immunotherapy with the use of anti-idiotypic antibodies. Furthermore, the finding of idiotopes shared by anti-HIV antibodies in outbred species presents a new target for active immunotherapy. Assuming that an anti-idiotypic antibody has been made against such shared idiotopes, these anti-Id could be used to boost or restimulate a beneficial immune response in seropositive individuals. Stimulating anti-Id could thus become an alternative to conventional therapeutic vaccines. Anti-Id have advantages over HIV Ag in active immunotherapy. One advantage is the escape from a clonal dominance of not effective or even virus-enhancing antibodies established during the chronic HIV infection.

In order that a given Id would be a clinically useful marker of disease or target for immunostimulation, the following two criteria must be met: 1) the expression of the idiotope in sera should be shared among the human outbred patient population and cannot be an individual or private idiotope. 2) This shared idiotope must show correlation with disease stage or the state of immunity against HIV infection. Therefore, the antibody expressing a given idiotope plays an important biologic function in the immunity against HIV infection, i.e., as neutralizing antibody or infectivity-enhancing antibody. Shared Id can also be found on antibodies directed to different epitopes of the disease causing Ag (35). In this situation, the shared idiotype may or may not be a disease-specific marker. The biologic role of idiotopes is determined by the degree of connectivity in the network. In other words, regulatory idiotopes are not unique chemical or serologic markers, but function in a regulatory capacity if they are highly connected and thus capable of controlling a biologically significant number of antibody-producing B cell clones (6, 35).

The generation of a panel of murine anti-idiotypic mAb against human polyclonal and monoclonal anti-HIV antibodies is described. Two of these anti-idiotypic antibodies are able to detect corresponding idiotopes expressed on heterologous human HIV+ serum antibodies. One anti-Id mAb (2A11) was derived from a fusion utilizing spleen B cells from BALB/c mice immunized previously with human anti=gp41 mAb (18, 37). The other anti-Id mAb originated from BALB/c mice immunized with human polyclonal HIVIG (19). Polyclonal HIVIG was chosen as Ab1 in order to obtain Ab2 that would detect broadly cross-reactive idiotopes on human HIV+ serum antibodies. Human monoclonal anti-HIV Ab1 as H2, however, induced a limited number of cross-reacting Ab2.

Idiotopes detected by the anti-idiotypic mAb are found in a number of patients and also in a pool of seropositive donors. In a related study by Miller et al. (38), certain anti-idiotypic mAb against individual B cell lymphoma Ig also react with Ig in normal serum. These anti-Id detect "shared idiotopes" expressed in an outbred population. There are anti-shared idiotopes reacting preferentially with idiotopes in HIV individuals. From preparative analysis of idiotope-positive Ig isolated from seropositive sera is seen an association with a unique epitope specificity. For example, the 1F7 idiotope-positive Ig binds to the core protein of HIV-1 and to a virus preparation that has been stripped off the envelope. On the other side, polyclonal antibody isolated from a 2A11 immunoabsorbent contains antibodies specific for gp120.

Preparative analysis of Id-positive Ab1 by Ab2 immunoabsorbent has been used previously (26) and allows the precise identification of the epitope specificity and biologic activity of Id-defined antibodies in sera or infected individuals. Garmendia et al. (26) generated rabbit anti-idiotypic antibodies (Ab2) against a mAb (Ab1) which neutralizes the FMDV. They isolated from virus-infected animals on Ab2 immunoabsorbent anti-FMDV antibodies that were capable of neutralizing FMDV in plaque reduction neutralization assay. It is important to distinguish this Id-defined Ab1 from conventional Ab1 that are typically made in an unrelated species or individual animal. The term of Ab1 (Id) is proposed to identify antibodies isolated from disease serum by an anti-Id (Ab2) immunoabsorbent. The Ab1 (Id) isolated from a single serum or pooled serum may be either restricted to an individual donor or found in several different donors and thus be shared. Demonstration of shared Ab1 (Id) is important for Id vaccine development because Ab2 that bind to a given shared Ab1 (Id) are likely to boost pre-existing Ab1 (Id) in infected individuals, as therapeutic Id vaccine, or induce Ab1 (Id) as prophylactic Id in naive individuals whose repertoire contains the Ab1 idiotypic specificity. Thus, the Ab2-induced Ab3 can be designated as Ab3 (Id), i.e., an Ab3 with the epitope and idiotypic specificity of the original Ab1.

From screening of panels of seropositive and normal sera with 1F7 and 2A11 individually different reactivity patterns were found with respect to possible disease correlation. It was excluded that the idiotype variability might be caused by different levels of total Ig in sera. Also, 1F7 did not react with serum specimens derived from patients with SLE and B cell lymphoma (FIG. 5A).

The finding of shared Id in AIDS patients that are associated with anti-HIV antibodies is unexpected. Shared cross-reactive Id have so far been demonstrated only in humans in autoimmune disorders such as SLE (39, 40) and rheumatoid arthritis (41, 42), and furthermore, in human antibodies specific to a capsular polysaccharide of *Hemophilus influenzae B* (43) and in antibody response directed to a high m.w. polysaccharide derived from *Pseudomonas aeruginosa* (44), respectively. The finding of shared idiotopes in AIDS-infected individuals may not be surprising considering the chronic nature of the immunodeficiency disease.

During the long infection phase, when a patient's immune system is still functioning, Ag-driven selection occurs, promoting certain high affinity clones that are closely related to germ-line gene encoded anti-HIV antibodies. Such germ-line-encoded antibodies may be the basis for the expression of cross-reactive or shared idiotypes as seen previously in the dominant T15 murine cross-reactive Id (45) and Id-restricted response specific for HIV-1 mouse anti-idiotypic mAb (46).

The variable light and variable heavy regions of the 1F7 antibody were determined and are set forth below.

1F7 Variable Light Chain (SEQ ID NO: 5)
L1: DIVLTNSPASLAVSLGQRATISC<u>KASQSVDYDGDSYMW</u>YQQ (SEQ ID NO: 6)
L2: KPGQPPKLLTI<u>AASNLES</u>GIPARFSGSGSGTDFTLNIHPVE (SEQ ID NO: 7)
L3: EEDAATYYC<u>QLCNEDPPT</u>FGAGTKQQQK 1F7 Variable Heavy Chain (SEQ ID NO: 8)
H1: QVTLKESGPGILQPSQTLSLTCSFSGFSLS<u>TSFMGVSW</u>IRQ (SEQ ID NO: 9)
H2: PSGKGLEWLA<u>HIYWDDDKRYNPSLKS</u>RLTISKDTSSNQDFL (SEQ ID NO: 10)
H3: KITSVDTRDTATYYCAR<u>RVSLTAYAMDY</u>WGQGTSVTVSS These amino acid sequences are labelled and used as probes for the detection of the HIV virus, particularly in sera. The probe can incorporate a detectable label as known in the art. For example, the label may be selected from chromophores, fluorophores, chemiluminescent materials and radioisotopes, that label the probe for detection. The sequences can be synthesized by methods known in the art.

Deceptive Imprinting in the Immune Response Against HIV-1

The clonal profile of anti-HIV-1 antibodies is established at the time of infection as part of a vigorous immune response against HIV-1, and remains stable during the infection process. This bias towards antibodies specific for the initially infecting clonal virus population, termed imprinting, is inappropriate for attempts of the infected host to control viral variants that subsequently emerge. The present inventors show that immunodominant epitopes on viral variants or recombinant proteins are selected that induce and maintain this deceptive state, and thereby remain unrecognized through a functional and cross-reactive hole in the B-cell repertoire.

The clinical problems associated with AIDS were initially reported 15 years ago and more than 12 years have passed since the human immunodeficiency virus (HIV-1), implicated in the infection leading to AIDS, was identified.[47,48] Despite enormous and expensive research efforts, no vaccine or cure for AIDS is anticipated in the near future. Conventional vaccine approaches fail in combating HIV-1, and a number of other human and veterinary pathogens, which use an array of immune-evasion strategies that are poorly understood.

An intriguing aspect of AIDS pathogenesis is the similarities between this infection and that of other chronic intracellular and blood-borne infectious agents.[51,52] Although these infections are not characterized by a non-immunogenic property of the infectious agent, they induce an initial immune response that, despite being robust, induces limited host protection. The working hypothesis for AIDS, therefore, would be that the immune response is misdirected and attenuated by the invading pathogen so as to allow a chronic active infection.

Normal immunological imprinting has evolved as a means of providing specific protective immunity against pathogens and is the underlying rationale for vaccine design. By contrast, abnormal or deceptive imprinting can be defined as a mechanism leading to a fixed state of immunity that fails to adapt to a changing, but closely related, pathogen. More specifically, this may be defined as the loss of the ability to discriminate antigen after the establishment of a strong primary immune response following infection or vaccination. This may result in impaired recognition of the selected, yet closely related, antigenic variants arising during the course of chronic infection, or at the time of primary exposure to the virus following vaccination. The consequence of such deceptive immunity would be the production of crossreactive, non-protective antibodies and/or clonally dominant cell-mediated immunity (CMI).

One of the striking biological properties of the HIV-1 virus is its ability to undergo spontaneous and rapid mutation, thereby producing a diverse spectrum of genomic and phenotypic variants with different virologic and antigenic properties. Therefore, it was surprising to find that a rather homogeneous viral population is selected rapidly both in vitro and in vivo following infection with a heterogeneous viral inoculum.[55] For example, in chimpanzees infected with HIV-1 IIIB stock, which contains three closely related variants, the first viral population to arise was clonally dominated by a single variant. The primary and secondary immune response (as measured by neutralization) was restricted to this initial variant, during which a switch to another dominant virus subpopulation in the inoculum occurred. Progressive viral isolates from the infected animals showed a pattern of slow, minor, yet progressive, genomic antigenic variations. These variants were subsequently shown to be immunologically crossreactive, yet failed to be neutralized by monoclonal and polyclonal antibody directed at the third hypervariable domain, V3 of the gp120 envelope glycoprotein.

Similar observations have also been made during the acute and chronic phases of HIV infection in humans.[56,57]

Genomic stability of the flanking and V3 regions was observed in the initial virus populations, lasting from 2–24 months. Limited studies have also shown which distant size mutations in this region can occur that influence the antigenicity of the V3 region.[53] It is hypothesized that this initial genomic and antigenic stability of the infecting virus population is a major cause of the strong imprinting effect on the immune response. However, by itself, this mechanism would not be expected to account fully for the observed restriction of clonal heterogeneity in the immune response. The deceptive aspect of imprinting probably arises from the sum of separate unique properties of the HIV-1 life cycle and the biochemical and immunogenic qualities of the viral envelope.[53,58] This also explains why there is limited sequence variation in patients with rather more average disease progression.

Evidence for a Restricted Clonal Heterogeneity of the Immune Response

Initial evidence for an oligoclonal antibody response to HIV antigens was provided as early as 1988 (Refs 59,60). Further studies[61,62] have demonstrated oligoclonal binding patterns by isoelectric focusing (IEF) in longitudinally obtained serum specimens from asymptomatic HIV-infected individuals and AIDS patients. In these studies, no change in the characteristic IEF spectrotype of anti-gp120 antibodies was observed over time. Furthermore, the IEF spectrotypes of serum anti-gp120 antibodies had banding patterns in the basic range[59,62], which reflect the complementary basic charge of the V3 domain of gp120. The immunogenic nature of the V3 domain is related to the high degree of basic residues, as well as its hydrophilicity and high potential for mobility, which appears to be preserved during selection and antigenic variation.

Oligoclonal antibodies are easily recognized in sera through their biased κ: λlight (L)-chain ratios, a consequence of normal isotype exclusion. Biased L-chain expression has routinely been observed in anti-gp120, anti-reverse transcriptase and anti-core antibodies, in contrast to antibodies produced by human myelomoas.[64] The ratio of L-chains expressed in response to other antigens, such as tetanus toxoid, was a normal 2:1 (κ:λ) in the cohort of HIV-infected individuals studied. Interestingly, anti-gp120 antibodies often have a λ L-chain bias (ratio<1:1), whereas anti-p24 antibodies frequently have a κ L-chain bias (ratio>2:1) (Ref. 64). In this context, it is noteworthy that in children with HIV infection, the maturation of the κ repertoire appeared to be blocked, leading to an overall λ bias of total IgG (Ref. 65) and a pronounced λ bias in nearly all antibodies directed to gp120 and V3 peptides of different IIIB, MN and SF2 strains.

Restricted anti-HIV-1 responses are also readily demonstrated by determining the utilization of antibody variable heavy ($V_H$)-chain gene families. In a "normal" antibody response, the size of the V-gene family is expected to be reflected in its utilization. In humans, the so-called $V_H3$-gene family is the largest among $V_H$-gene families, and the majority of anti-bacterial and anti-polysaccharide antibodies in humans are encoded by this family.[62,67] By contrast, it has been observed that anti-gp120 and anti-p24 antibodies, affinity purified from serum of individuals infected with HIV-1, are often depleted in antibodies encoded by the $V_H3$-gene family.[64] In addition, the immunodominant V3 loop and its flanking regions bear sequence homology to the framework and complementarity-determining regions of human immunoglobulins.[68] This Ig-like domain of gp120 appears to be selected for an immunological function in order to permit HIV-1 entry into the immune regulatory network.[69]

Another finding suggests that the gp120 protein has a B-cell superantigen (SAg)-like activity that has affinity to antibodies encoded by the $V_H3$-gene family.[70] Since SAgs can exhaustively stimulate lymphocytes to undergo apoptosis, the anti-gp120 antibodies from chronically infected individuals are expected to be deficient in certain $V_H$-family antibodies and enriched in others. Finally, analysis of idiotypes in the anti-gp120 response has indirectly indicated clonal restriction of circulating anti-gp120 antibodies, which were affinity purified on anti-idiotypic antibody-conjugated Sepharose from pooled serum of different HIV-infected individuals and analyzed by IEF (Ref. 71). In this study, the idiotype-positive anti-gp120 antibodies frequently show an oligo- or monoclonal IEF pattern.

Biology of Clonal Immune Dominance

Normal immune responses are highly diverse and involve a large number of different B- or T-cell clones. So-called "naturally dominant" immune responses are observed in some responses to bacterial or viral pathogens.[62,67] In certain diseases, especially autoimmune diseases, a restricted antibody response has been reported.[72] A striking biological quality of the clonally restricted response is the difficulty in broadening it to the level of a "normal" polyclonal response. The restricted response in HIV-1-infected individuals is persistent over years of observation in a given patient.

At the T-cell level, Rowley and Stach[73] have shown that an ongoing, strong, allogeneic cytotoxic Y lymphocyte (CTL) response can suppress a subsequent CTL response to other challenges. The suppressive effect is mediated by transforming growth factor β (TGF-β) complexed to immunoglobulins.[74] In a study of the CTL response of HIV-1 infected humans, a restricted capacity to lyse sequence-specific proteins from the virus was observed (P. R. Johnson, A. Kalams, B. Walker et al., unpublished). A similar restriction in T-cell proliferation assays has been observed for 75% (n=235) of HIV-1 recruits in the Walter Reed immunotherapy trial before boosting, as well as in all of three laboratory workers infected with HIV-1 who were tested in this way (D. Brix, M. Nelson, R. Redfield, M. Reitz, D. Bruce and W. Blatner, unpublished). In the majority of cases studied, normal T-cell proliferation profiles were observed for recall or new test antigens such as rabies and/or tetanus.

For B-cells, different lymphokines may have similar effects on the antibody response. Recently, high levels of interleukin 4 (IL-4), produced by T helper 2 (Th-2) lymphocytes, have been reported in HIV-1 infected individuals, and this appears to be linked to disease progression.[75] Lymphokines produced by Th2 cells also appear to be associated with immune deficiency in mouse AIDS (MAIDS) (Ref. 76), since Th2-knockout mice are resistant to infection with the MAIDS leukemia virus. Cytokine imbalance by itself has been suggested, as a major factor in the pathogenesis of AIDS (Ref. 76). Lymphokines produced by Th2 cells, such as IL-4, IL-5 and IL-6, are stimulators for B cells and could help to establish clonally selected antibody responses that would not benefit the resolution of disease. Continued high-level production of Th2-type lymphokines during infection could maintain clonal expansion of B-cells, leading to high levels of "useless" antibodies. Thus, the notion of clonal imprinting described here would support, in part, the concept suggested by Salk et al.[77] that suppression of Th2-mediated help by upregulation of Th1-dependent CMI may be beneficial for HIV-infected individuals.

According to this concept, the primary antibody response to the initial viral burst that occurs immediately after infection becomes clonally dominant and may limit, suppress or prevent the effective triggering of other clones that have the potential to respond to virus variants selected subsequently. This creates a situation in infected individuals whereby such antibodies may select for antigenic variants, which remain unrecognized due to a functional hole in the B-cell repertoire, and thus fail to neutralize adequately any but the infecting parental virus variants. This has been described as "clonal dominance" or "repertoire freeze".[78] The events that are envisaged to lead to deceptive imprinting, and the failure of the immune response directed against viral variants, are listed in Box 1 below.

---

BOX 1
Proposed steps and events leading to deceptive immunological imprinting

---

(1) Initial infection and replication of a genetically homogenous virus population.
(2) Vigorous primary immune response together with strong inappropriate production of lymphokines such as transforming growth factor β (TGF-β), interleukin 4 (IL-4) and interferon α (IFN-α).
(3) Enhancement of primary immune response vta a superantigen-like property of the virus envelope or $V_H$Ig-like mimicry of the shed viral envelope.
(4) Suppression of secondary clonal responses of T and B cells by viral products or lymphokine(s): clonal imprinting occurs.
(5) Spontaneous mutation and selection of viral variants that continue to stimulate the originally expanded, still crossreactive, B-cell clones: reinforcement of clonal imprint occurs.
(6) Continued emergence of escape variants caused by a failure of the immune repsonse to recruit immune-competent lymphocytes.
(7) Failure of the immune system to control the replication of escape variants: chronic active infection and progressive destruction of immune function occurs.

---

Whereas immunological imprinting against pathogens that are antigenically more stable will provide effective immune memory recall, and thus protection, imprinting against those pathogens that are able to undergo rapid antigenic drift, such as HIV-1, tricks the immune response into producing relatively useless antibodies.

Vaccine trials provide an interesting case for consideration. It is possible that subunit vaccines or live HIV-1 vaccines induce similar deceptive imprinting to that observed in wild-type infection. Thus, vaccines only protect against a perfectly matched virus population and could not protect against virus variants that would require the response of B-cell clones different from those primed by the vaccine. Since the infecting inoculum in "normal" infection comprises different quasi-species, any vaccine that induces imprinting would be reinforced during infection.

While the crossreacting viral variants are neutralized, other non-crossreacting variants are expected to infect the individual, who is severely restricted in this ability to respond to non-crossreacting virus. Thus, disease could be accelerated by this mechanism. This has been observed experimentally[79], and may have occurred in recent vaccine trials based on recombinant gp120, in which several high-risk volunteers seroconverted.[49]

Figure 9:
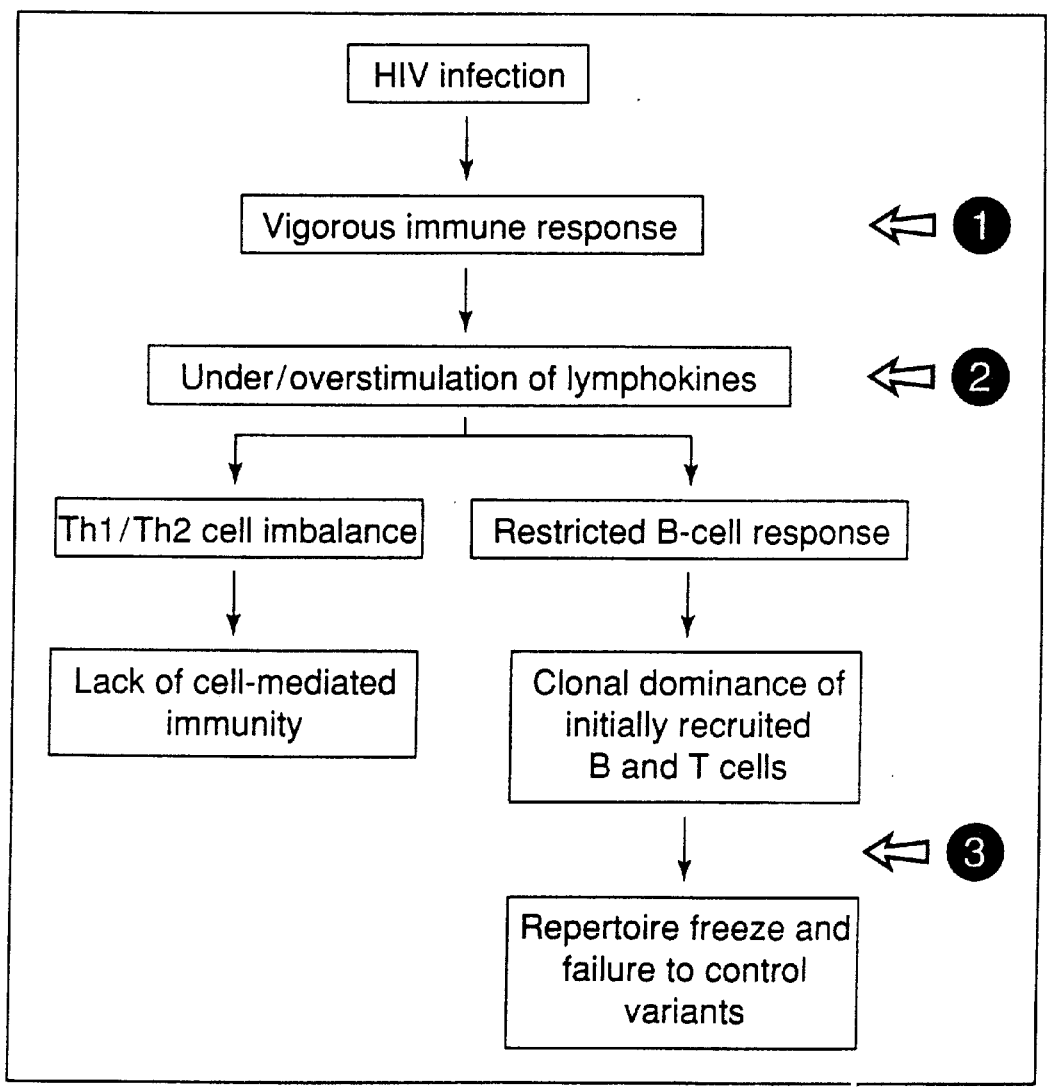
Figure 11A:
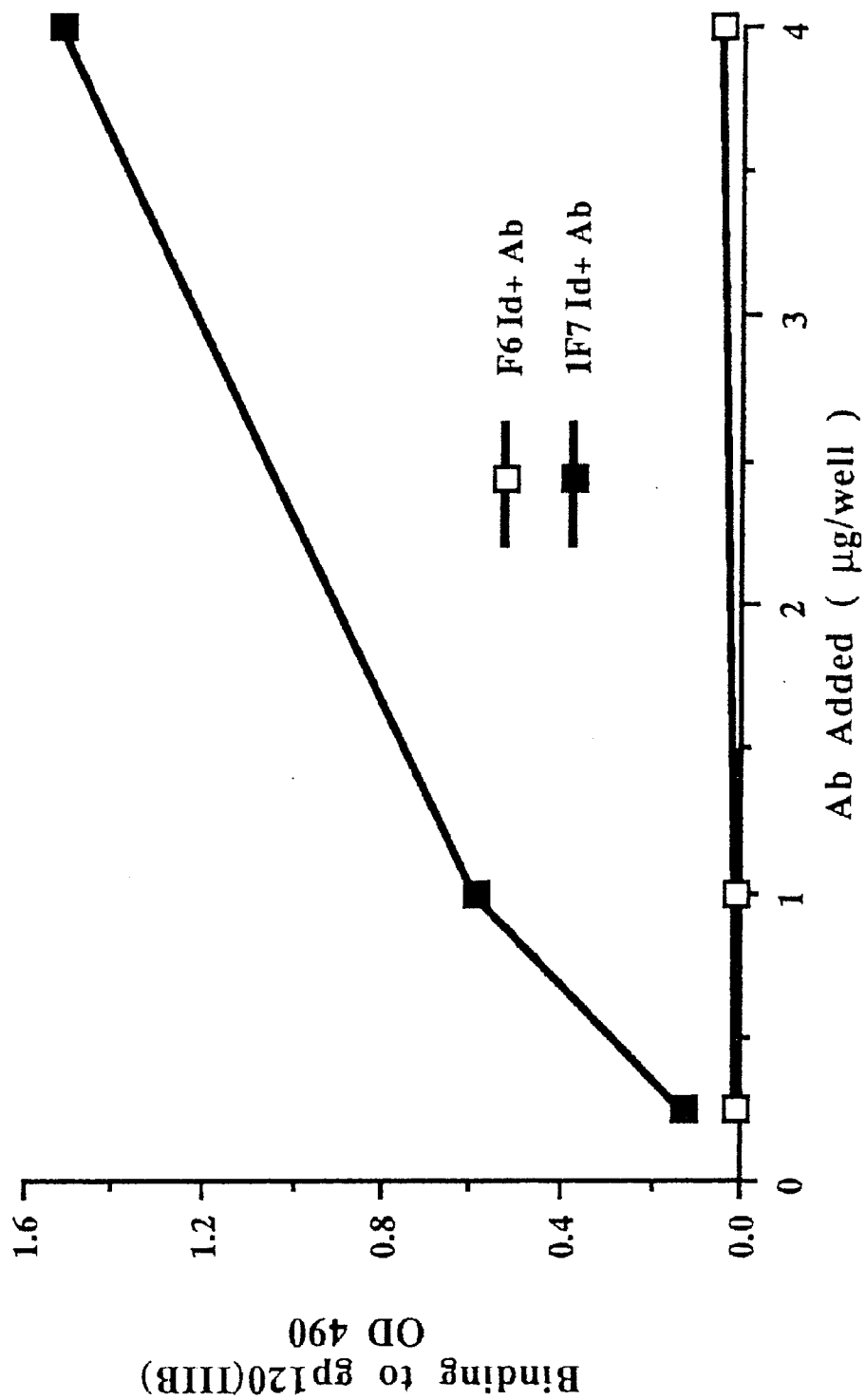
Figure 11B:
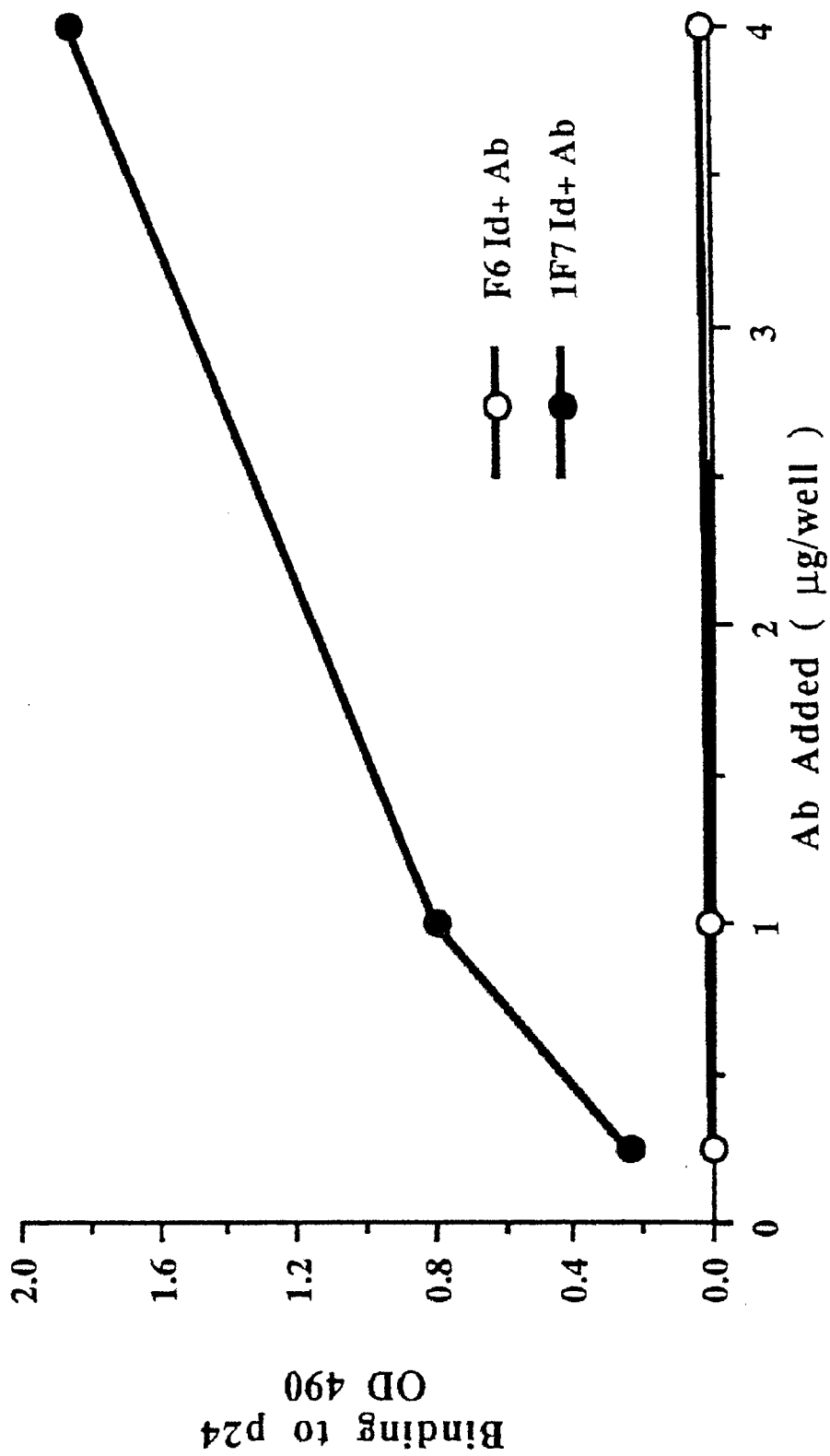
Figure 11C:
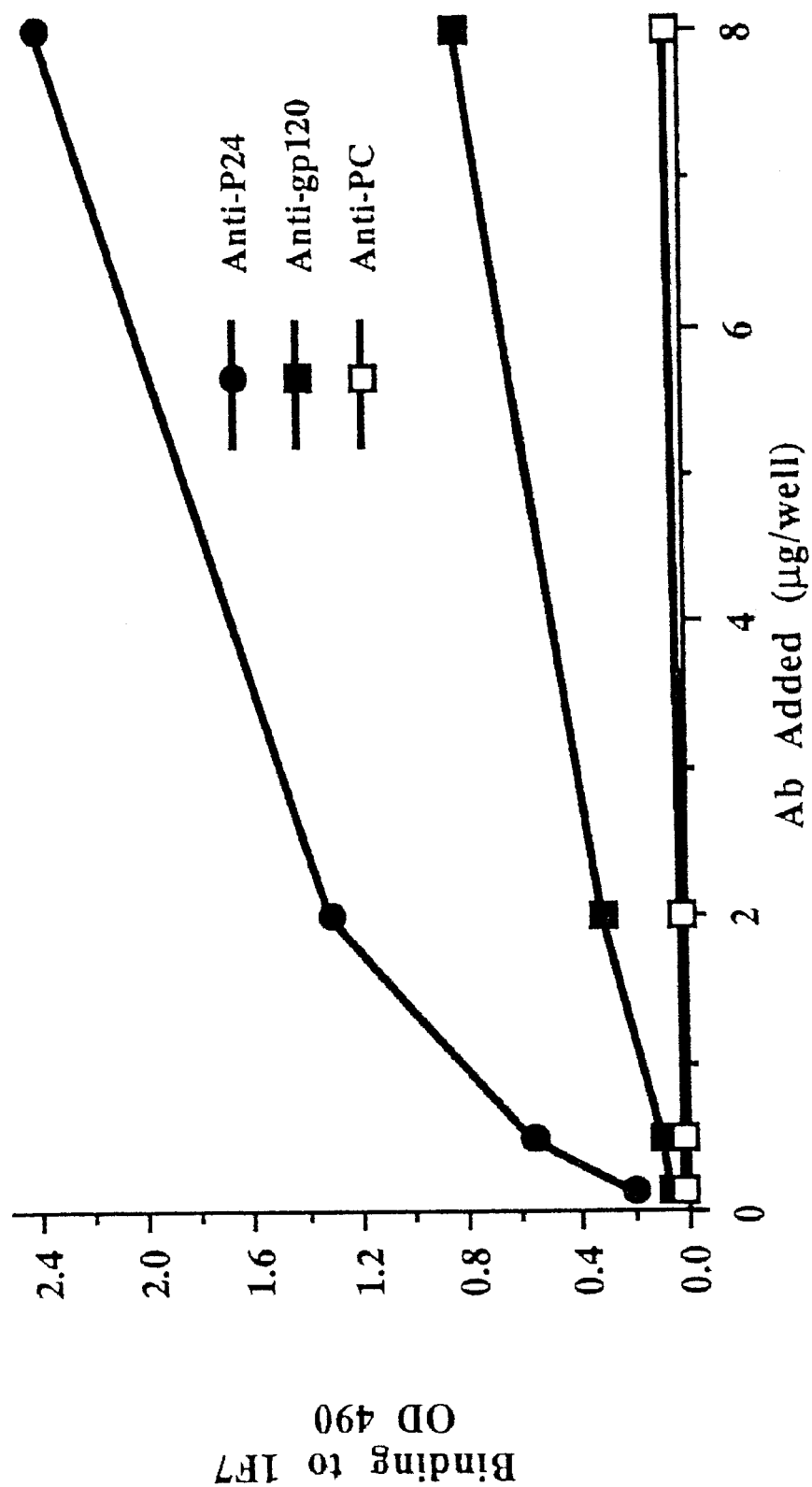

The events described in Box 1 are several ways by which to prevent deceptive imprinting mechanisms. Major strategies for intervention at different stages of the pathobiology of HIV-1 infection are shown in FIG. 9. One approach to prevent deceptive imprinting by HIV-1-derived vaccines would be to mask the major V3 epitopes by glycosylation.[80] At the time of infection, and shortly after infection, selective cytokine therapy could prevent or reverse the Th1-to-Th2 shift as proposed by Salk et al.[77] In animals, clonally dominant antibody responses can be suppressed by administration of anti-idiotypic antibodies.[81,82]

Anti-idiotypic antibodies, or particular sequences, or functional variants thereof, against crossreactive and widely shared idiotypes on anti-HIV-1 antibodies are used to suppress the clonally established response in HIV-1-infected individuals, and thus allow the appearance of a "normal" polyclonal viral-directed antibody response.

According to the present invention, anti-idiotypic antibody 1F7, or compositions comprising the monoclonal antibody 1F7 variable, light chains and heavy chains and functional equivalents thereof are used to suppress the clonally established response in HIV-1-infected individuals, and thus allow the appearance of a "normal" polyclonal viral-directed antibody response.

Further, the anti-idiotypic antibody 1F7, or compositions comprising the monoclonal antibody 1F7 variable, light chains and heavy chains and functional equivalents thereof, of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Additives are selected such that they do not interfere with the functional properties of the antibody or sequence segments.

Pharmaceutical compositions (wt %) of the active ingredient with a carrier or vehicle may comprise from about 1 to 99% and preferably about 1 to 20% of active ingredient. In a preferred embodiment, the effective dosage amount is 10 to 500 mg per dose to patient, as required to achieve anti-clonotypic suppression. For clonotypic stimulation (active immunization) a lower dose, preferably about 0.5 to about 500 mg, more preferably 0.5 to 5 mg, of 1F7 in adjuvant per inoculation per patient can elicit B-cells to respond broadly to HIV-1 antigens. The adjuvant may be selected to boost specific 1F7 immune response, such as adjuvants known in the art.

Either fluid or solid unit dosage forms can be readily prepared for oral administration. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule. Suspensions, syrups and elixirs may be used for oral administration of fluid unit dosage forms. Pharmaceutical compositions for parenteral and suppository administration can also be obtained using techniques standard in the art.

The above and other drugs can be present alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. The required dose when administered parenterally, may be administered 1 or 2 times a day for an adult human.

Stimulation of HIV-1 Neutralizing Antibodies in SHIV (IIIB)-infected Macaques

Abbreviations

SHIV-HXBc2 (IIIB), Simian Human Immunodeficiency Virus-HXBc2 (IIIB); HIV-1, Human Immunodeficiency Virus Type 1; SIV, Simian Immunodeficiency Virus; LAV, Lymphadenopathy Associated Virus; TEPC183, mouse myeloma; 1F7, designated idiotope; mAb, mouse monoclonal antibody; gp120/160, HIV-1 glycoprotein 120/160; p24, core protein 24; RT, reverse transcriptase; TCID50, tissue culture infectious dose yielding 50% positive cultures, HIVIG, Human pooled immunoglobulin type G from HIV-1 infected blood donors; HRPO, horseradish peroxidase.

To test the potential of mouse monoclonal antibody (mAb) 1F7 as a therapeutic anti-clonotypic antibody in HIV-1 infected patients, we used the SHIV-(IIIB) macaque infection model which mimics several immunological and pathological characteristics of HIV-1 infection in humans.

Four healthy SHIV-infected macaques expressing the 1F7 marker on anti-gp120 antibodies were selected for this study. Three monkeys of this group were immunized several times with the murine mAb 1F7 i.v., and one monkey received as control an isotype matched antibody, TEPC183. No serious side effect or allergic reaction was encountered. Blood collected before, during the immunization and over several months afterwards were analyzed for neutralizing antibodies. Significant increases in breadth and potency of HIV-1 neutralizing antibody titers to one or more virus strains were detected in all three of the 1F7 immunized macaques, but not in the control monkey immunized with TEPC183.

These results show that an antibody, recognizing a public idiotope associated with anti-HIV-1 antibodies, can function in chronically infected primates as an anti-clonotypic immunogen to boost antibodies which neutralize homologous and heterologous virus strains. This study represents a first step towards the preclinical evaluation of 1F7 as a therapeutic AIDS vaccine.

Introduction

The potential of 1F7 to boost or induce de-novo neutralizing immunities in infected individuals was tested in a non-human primate model (*Macaca mulatta*). The monkeys selected for this study were chronically infected with a chimeric virus expressing the HIV-1 HXBc2 envelope protein on a SIVmac backbone (SHIV-HXBc2), and had produced antibodies recognizing the viral envelope protein, HIV-1 gp120 (85).

The SHIV/macaque model is well suited to vaccine-related immunological studies. Macaque immunoglobulins are highly similar to their human homologues (86), and the infecting virus has been engineered and cloned so that all macaques used for this study have received identical inocula of virus. The envelope derives from HIV-1 isolates and therefore expresses serologically relevant neutralization epitopes. In recent studies we have shown that 1F7 idiotope is present on HIV-1 anti-gp120 antibodies produced by many SHIV infected macaques (87).

In the present study we describe the changes in virus neutralizing antibody activity induced by "vaccination" with mAb 1F7 in four macaques chronically infected with SHIV-HXBc2 (SHIV-IIIB). Two macaques vaccinated with 1F7 responded with a boost of antibodies neutralizing the infecting, homologous HIV-1 IIIB strain, and more significantly, all three 1F7-treated macaques responded with a significant increase of antibodies neutralizing the heterologous HIV-1 MN strain. Therefore, therapeutic "vaccination" with an anti-clonotypic antibody can increase the potency and broaden the breadth of virus neutralizing antibodies in a relevant non-human primate model for HIV-1 infection.

EXAMPLE 16

Simian/Human Immunodeficiency Virus Construction and Infection of Rhesus Monkeys The design and preparation of SHIV-HXBc2 (hereafter, SHIV-IIIB)stocks are described elsewhere (85). The rhesus monkeys (*Macaca mulatta*) used in this study were maintained at the New England Regional Primate Research Center in accordance with the guidelines of the Committee on Animals for the Harvard Medical School and the Guide for the Care and Use of Laboratory Animals (88). Juvenile macaques were infected by intravenous inoculation with 400 TCID50 of SHIV-IIIB. The animals selected were infected two years prior to the onset of this study. Infection of all animals was confirmed by serologic and virologic assay.

EXAMPLE 17

Selection of SHIV-IIIB Infected Macaques for 1F7 Inoculation

Six macaques infected with SHIV-IIIB for two years were repeatedly monitored for anti-HIVgp120 antibodies and 1F7 idiotype (Id) expression during a period of two months (87). Four animals that showed consistent titer of anti-gp120IIIB antibodies and 1F7-id expression over that time period were selected for in vivo inoculation with mouse monoclonal antibody 1F7 or the isotype control mouse myeloma TEPC183. The selected animals were assayed again for anti-gp120 antibodies and 1F7-id expression before in vivo inoculation of mAb 1F7 or TEPC. The monkeys had low virus load throughout the study as determined by a commercial p27-antigen test at the threshold of detection level (data not shown). The animals selected for the study had a normal $CD4^+/CD8^+$ cell ratio which ranged from 1.2 to 1.6. No animals showed any signs of disease.

EXAMPLE 18

Preparation and Purification of mAb 1F7 and TEPC 183

The murine monoclonal anti-idiotypic antibody 1F7 (IgM, kappa) was generated previously by immunizing Balb/c mice with pooled HIVIG as described (89). The 1F7 hybridoma protein product bound to human polyclonal and monoclonal antibodies derived from HIV-1 infected individuals captured by HIV-1 antigen, but not to immunoglobulin from HIV-1 seronegative donors (89,90). The hybridoma was subcloned four times, the subclone 1F7 was amplified as ascites in Balb/c mice and purified on a goat anti-mouse IgM-Sepharose 4B column as described earlier. Some batches of monoclonal Ig were obtained using a modified purification procedure for 1F7. The cells were injected intraperitoneally (i.p.) into SCID mice free of mouse Ig. The protein in ascites was precipitated by 50% saturated $(NH)_2SO_4$ and centrifuged at 10,000 rpm for 30 min. The precipitate was dissolved in 10 ml 0.01 M PBS and aliquoted into pyrogen-free, sterile plastic vials. Endotoxin concentrations were below the threshold pyrogenic dose (1 ng of endotoxin per dose of kg body weight) as determined in a commercial quantitative test kit (91). Commercially obtained TEPC183 ascites (Sigma) was purified as described above. TEPC183 is a mouse myeloma and served as isotype control antibody (IgM, κ) for 1F7 in ELISA (87).

EXAMPLE 19
Anti-HIV-1 gp120 Antibody and 1F7 Idiotope Expression in Plasma of SHIV-IIIB Infected Macaques Immunoglobulins in plasma recognizing HIV-1 envelope glycoproteins were detected by ELISA described in detail elsewhere (87,89,90) using HIV-1 rgp120 IIIB or HIV-1 rgp120 LAV as antigen. Recombinant rgp120 IIIB was purchased from Intracel Corporation, (Cambridge, Mass.) and recombinant gp120 LAV was obtained through the AIDS Research and Reference Reagent Program (Division of AIDS, NIAID, NIH). Recombinant gp120 IIIB and rgp120 LAV are closely related and are therefore treated in the present report as one antigen. HIV-1 gp120 LAV envelope protein was a full-length, glycosylated recombinant protein derived from the env gene of HIV-1, produced in insect cells using the baculovirus expression system and purified under conditions designed to preserve biological activity and tertiary structure (MicroGeneSys).

Briefly, microplate wells were coated with 2 μg/ml of HIV-1 rgp120 IIIB or LAV and incubated at 4° C. overnight. After washing three times with PBS-Tween20, the wells were blocked for 2 hours with 120 μl/well of 3% BSA. Plates were washed three times as above and 100 μl/well of diluted duplicates or triplicates of macaques' plasma specimens were added and incubated for another 2 hrs. After additional three washes, 1:4000 diluted goat anti-rhesus IgG-HRPO (Southern Biotechnology) was added and incubated for 2 hrs. The binding antibodies were visualized by adding 50 μg/well substrate solution (OPD, Sigma). The enzyme/substrate reaction was stopped by 30 μl 4N sulfuric acid. All incubations were at room temperature unless otherwise noted. O.D. value was measured at absorbency of 490 nm.

1F7-Id expression on antibodies against HIV-1 gp120 was detected with a modified sandwich ELISA (87,89,90). Briefly, microplate wells were coated with rgp120 and blocked as described above. After washing three times, 100 μl/well of diluted plasma specimens were added and incubated for 2 hrs. Plates were washed three times and is 200 μg/well mAb 1F7 or TEPC183 was added at 2 μg/ml and incubated for another 2 hrs. After washing three times, 1:4000 diluted goat anti-mouse IgM-HRPO was added and incubated for 2 hours. mAb 1F7 or TEPC183 binding was visualized as described above. The mean of duplicate O.D. readings plus/minus standard error of the mean were used for data presentation in the graph.

EXAMPLE 20
Immunization of the Monkeys with Murine Monoclonal Antibodies

Three monkeys were immunized with purified, sterile mAb 1F7 intravenously. Two monkeys (designated 149-92 and 337-91) received twice-weekly injection of 5 mg mAb 1F7 resulting in a total dose of 20 mg 1F7. A third monkey (42-93) received four injections with the isotype matched antibody control mouse mAb TEPC183 (IgM, κ), following the same protocol of injections twice a week. A fourth monkey (441-92) was injected twice-weekly with 5 mg 1F7 delivering a total dose of 30 mg 1F7. Blood samples were collected immediately prior to each injection and then weekly, bi-weekly and monthly. Plasma was obtained by centrifugation (400× g) of EDTA-anticoagulated venous blood samples, and stored frozen at −200° C. until use. Prior to ELISA, plasma samples were heat-inactivated (56° C. for 40 minutes) to kill residual virus.

EXAMPLE 21
Determination of Neutralizing Activity of Antibodies Against HIV-1 IIIB and MN A quantitative syncytium forming microassay was employed for detection of the virus neutralizing antibody response (92,93). Neutralization titers were determined using two HIV-1 strains, HIV-1 IIIB and HIV-1 MN. A virus-syncytial sensitive clone of CEM cells (CEM-SS) develops quantifiable, adherent syncytia (syncytial forming units; SFU) on a background of confluent, normal CEM monolayer in 4 to 6 days. Total infectious virus can be accurately determined in this assay; results using standard HIV-1 stocks showed a close association with p24 antigen test.

Serial dilution of plasma specimens taken at time points before and after injection with 1F7 mAb or TEPC183 from the four SHIV-IIIB infected macaques were screened for antibody neutralizing activity via inhibition of syncytium formation. Briefly, CEM-SS cells are plated as described (92) and incubated with duplicates of various preincubated virus/plasma dilution (50 μl/well) at 37° C., 5% $CO_2$, for 60 min. Neutralization was calculated as the virus surviving fraction ($V_n/V_0$) from the reduction of syncytial-forming units (SFUs) and represented as the number of syncytia induced by HIV-1 ($V_n$) in the presence of serial two-fold dilution of serum divided by the number of total added virus-induced SFUs ($V_0$).

EXAMPLE 22
Statistical Analysis of Antibody Responses

Viral antigen binding antibodies and HIV-1 IIIB and MN neutralizing antibody titers were subjected to statistical analysis to determine the significance of changes observed after vaccination with mAb 1F7 or control mAb TEPC.

Plasma neutralization activity was determined from viral neutralization curves for all animals on given days. Daily curves were fit with a quadratic regression model, $Y=b_0+b_1X+b_2X^2$, in which $Y=V_n/V_0$, the viral surviving fraction, and X= the log plasma dilution. The $b_0$ parameter describes the Y-intercept of the graph that is the most diluted plasma tested (no neutralizing antibody activity, i.e. $V_n/V_o=1$). The $b_1$ parameter describes the "slope" of the curve (how rapidly the curve is falling). The $b_2$ parameter describes how much the curve levels out at higher concentration. Two or more curves can be compared by determining whether these parameters across curves are the same or different statistically. If the $b_0$, $b_1$, and $b_2$ parameters do not differ significantly across the curves (i.e., $p>0.05$), the curves will look similar. On the other hand, if one or more of the parameters across the curves differ significantly ($p<0.05$), the graphs will look different. For each animal, we compared daily curves to baseline ("pre-bleed") curves (or each other) with the analysis of covariance (Anova). In this framework, hypotheses regarding significant differences in $b_0$, $b_1$, and $b_2$ parameters were performed based on the "extra sums of squares" principle (94) or the principle of "conditional error" (95,96). In practice, we found that all hypotheses for significant differences in neutralization curves were significant when reduced to determine whether there existed significant differences in the $b_0$ parameters (intercepts) of the two curves being compared.

Results
Expression of 1F7-positive Antibodies in SHIV-IIIB Infected Macaques

Figure 12:
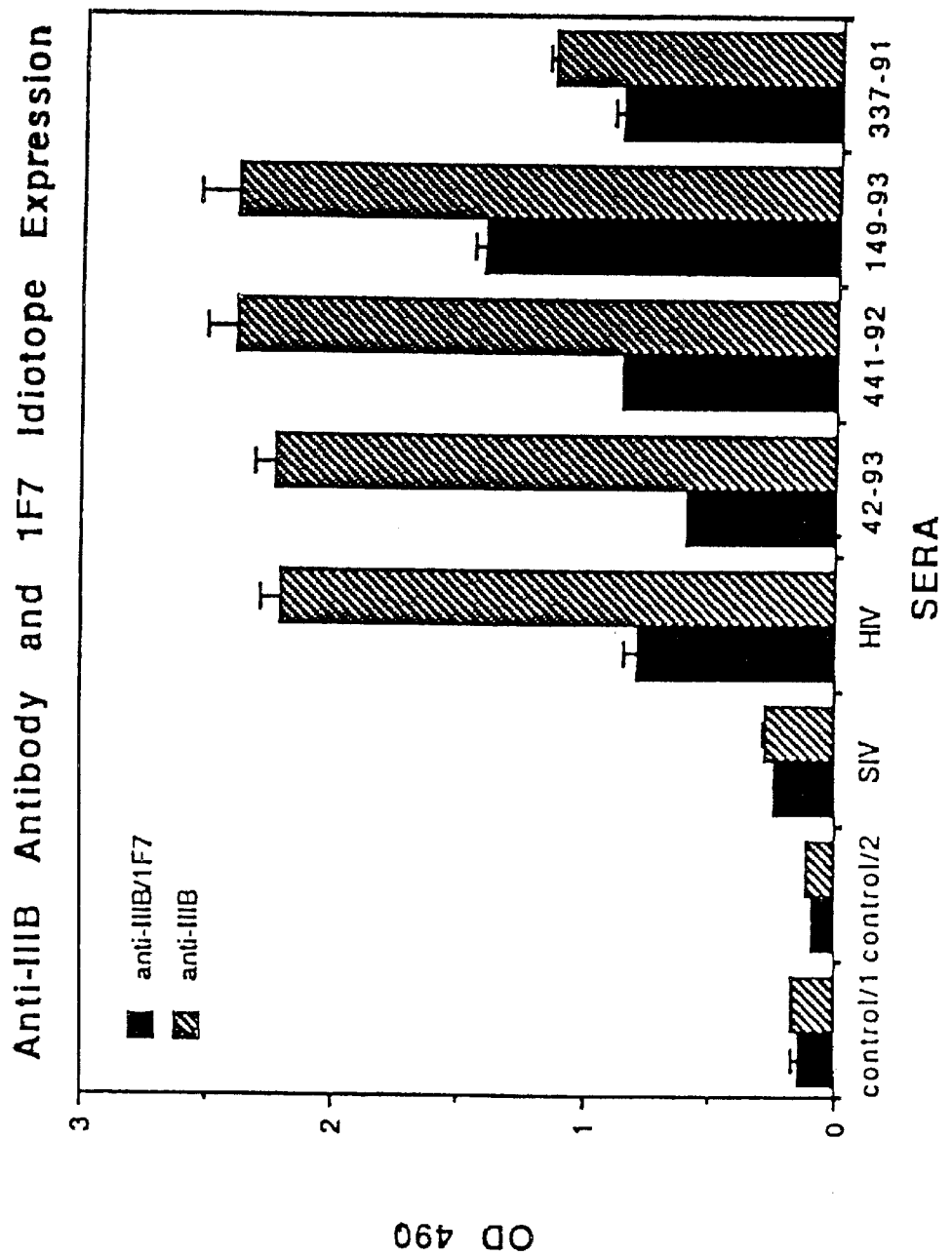

In a recent study we screened six SHIV infected rhesus macaques for the presence of anti-envelope antibodies (LAV and IIIB) in blood (87). We found that two thirds of the SHIV-IIIB-infected monkeys express the 1F7 marker on anti-HIV-1IIIB or LAV antibodies. Four of these animals were selected for in vivo treatment (immunization) with mAb 1F7. All four monkeys contained anti-HIV-1 gp120 IIIB antibodies which were even 1F7-id positive prior to immunization with mAb 1F7 (FIG. 12). As a negative control for the assays plasma from a SIV infected macaque which does not contain antibodies against HIV-1 gp120 IIIB is presented. Binding of 1F7-id-expressing serum antibodies directed against HIV-1 gp120IIIB derived from a human HIV-1 positive individual is shown as positive control to demonstrate the specificity of the assay measuring anti-gp120IIIB antibody. Furthermore, normal non-infected human and macaque serum showed no reactivity in the 1F7/IIIB ELISA (FIG. 12). In FIG. 12 antibodies binding to gp120IIIB are shown together with the amount of 1F7 Id detected from monkeys 149-92, 42-93, and 441-92 assayed 3 months before the vaccination. Since the ELISAs for anti-envelope and 1F7-id use different reagents in part the optical density (O.D.) values are not quantitatively comparable.

These results indicate that the four selected monkeys produced significant amounts of 1F7-id expressing anti-envelope antibodies and were therefore suitable for anti-clonotypic stimulation using the mAb 1F7 as therapeutic vaccine.

Immunization of Three Monkeys with mAb 1F7 and One Monkey with Control Antibody TEPC183

Three 1F7-Id positive infected monkeys were injected with mAb 1F7 intravenously. Monkeys 149-92 and 337-91 each received intravenous injections of 5 mg mAb 1F7 twice a week resulting in four injections and a total dose of 20 mg 1F7. Monkey 441-92 was injected with 5 mg mAb 1F7 twice-weekly delivering a total dose of 30 mg 1F7. The fourth monkey 42-93 received four injections with the isotype matched antibody control mouse mAb TEPC183 (IgM, κ), following the same protocol of twice-weekly injections.

Analysis of Antibodies Against HIV-1 Envelope

Blood samples were obtained from all monkeys prior to injection and afterwards, as specified below. All animals were observed for up to 9 months after the vaccination. No allergic or toxic reactions to the murine monoclonal antibodies (mAb) were observed.

Figure 13A:
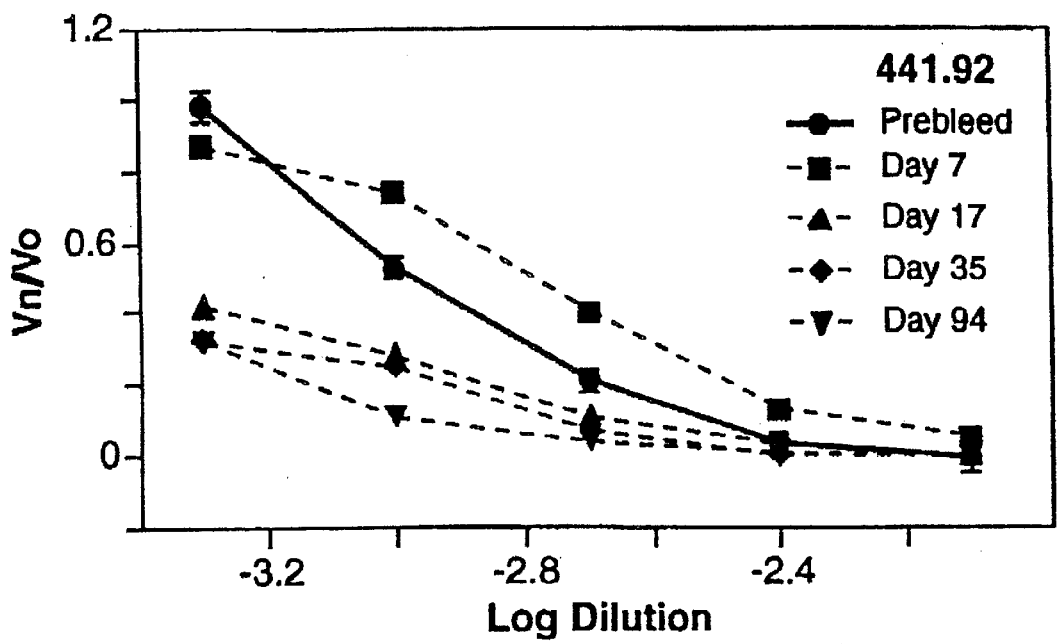
Figure 13B:
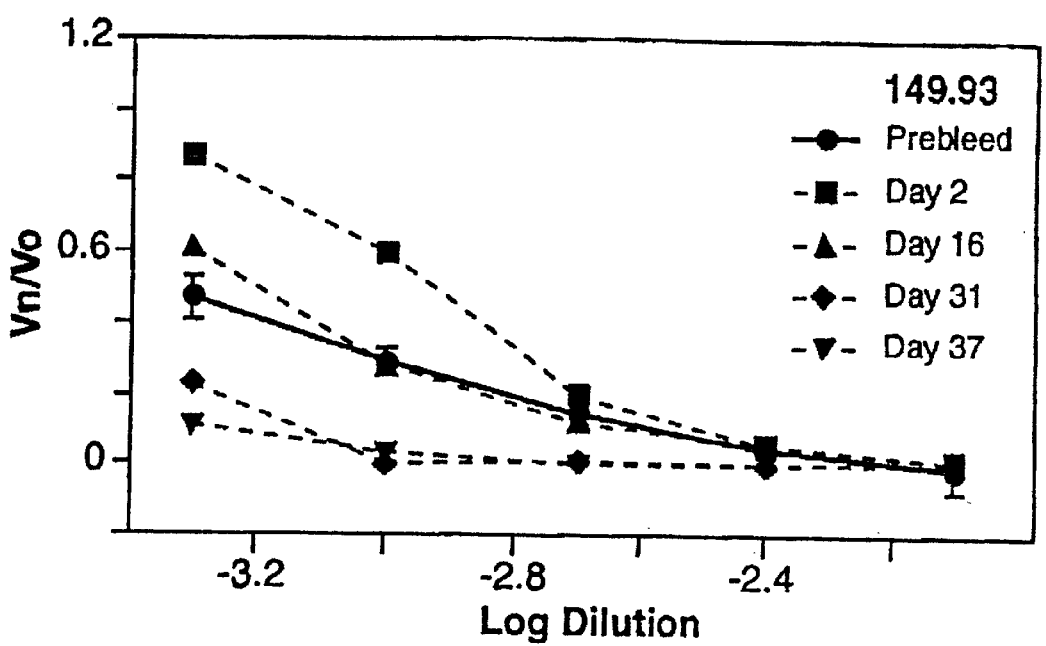
Figure 13C:
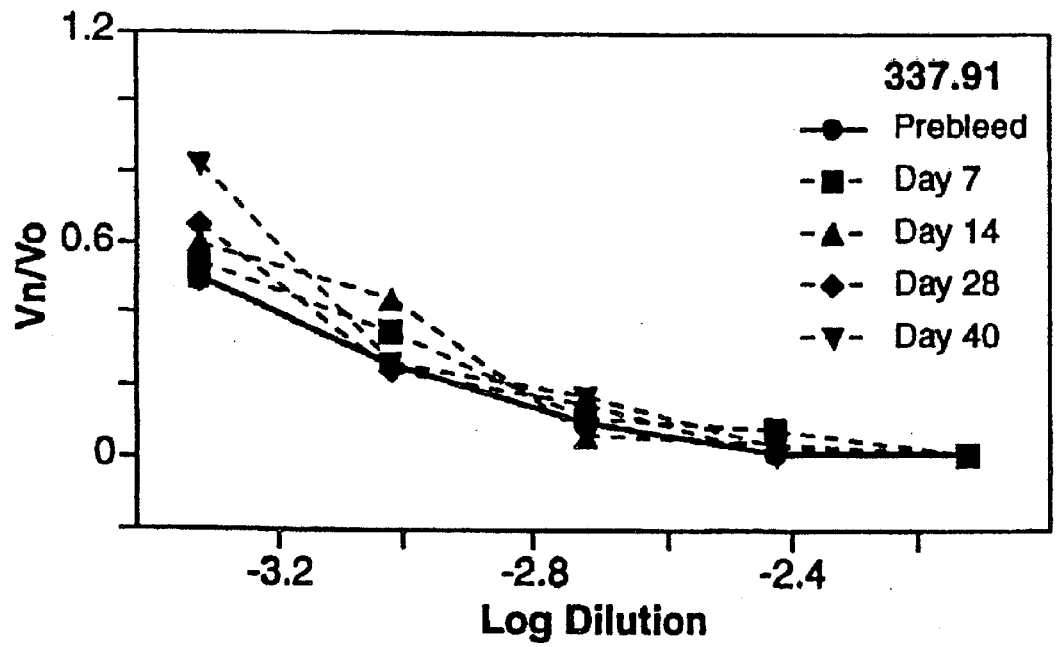
Figure 13D:
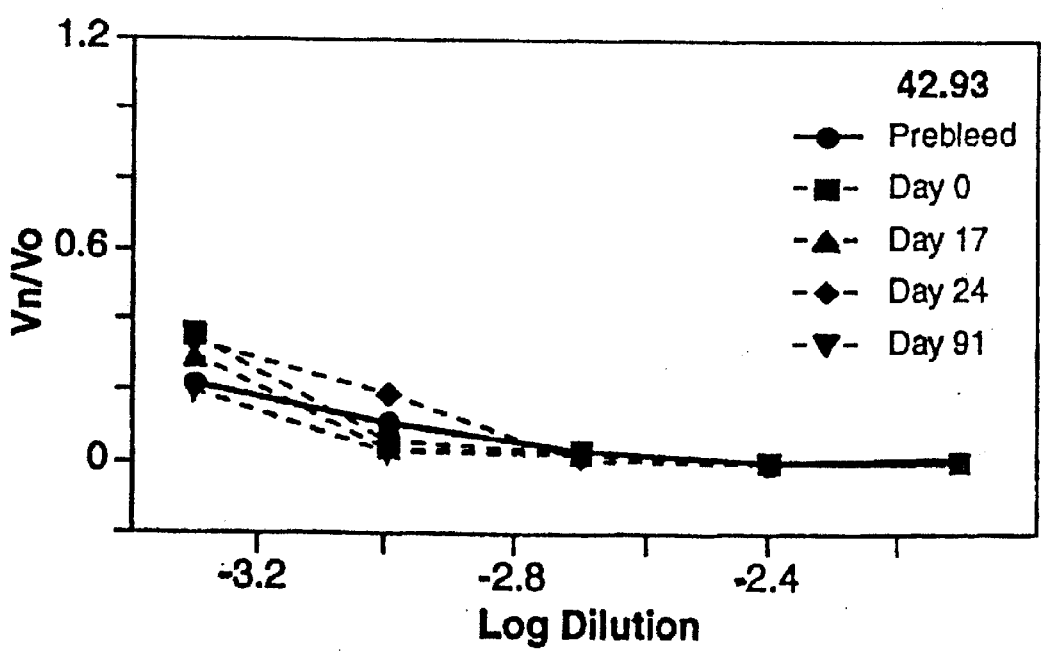

Sera were assayed in ELISA against IIIB recombinant gp120 and for 1F7 expression on anti-gp120 IIIB antibodies as described (87,90,97). The data from the pre-bled are compared with readings of the peak response from each monkey (see FIG. 13). All monkeys vaccinated with 1F7 showed an increase of anti-gp120 titers (FIGS. 13A, B and C), while the control TEPC 183 vaccinated monkey produced no increase of anti-IIIB titer (FIG. 13D). The 1F7 positive anti-IIIB titers also increased after 1F7 vaccination, although the increase was not as pronounced as in the anti-IIIB titer.

Analysis of Virus Neutralization Potency

Bleedings from the three monkeys injected with mAb 1F7 and the TEPC183-injected control monkey were analyzed before, during and after the vaccination regimen. Serial dilution of plasma specimens collected at different time points during the observation period were analyzed for virus neutralizing antibody activity using a quantitative syncytia forming microassay (92) and HIV-1 strains IIIB and MN. The neutralization activity for HIV-1 IIIB and for HIV-1 MN was derived from five plasma dilution at day 0 (prebleed), and four times after day 0 for each macaque. To assess the significance of mAb 1F7 inoculation, neutralization curves were constructed on different days and compared to baseline (pre-bleed) according to the procedures outlined in the statistical analysis section.

a) Monkey 441-92

Figure 14A:
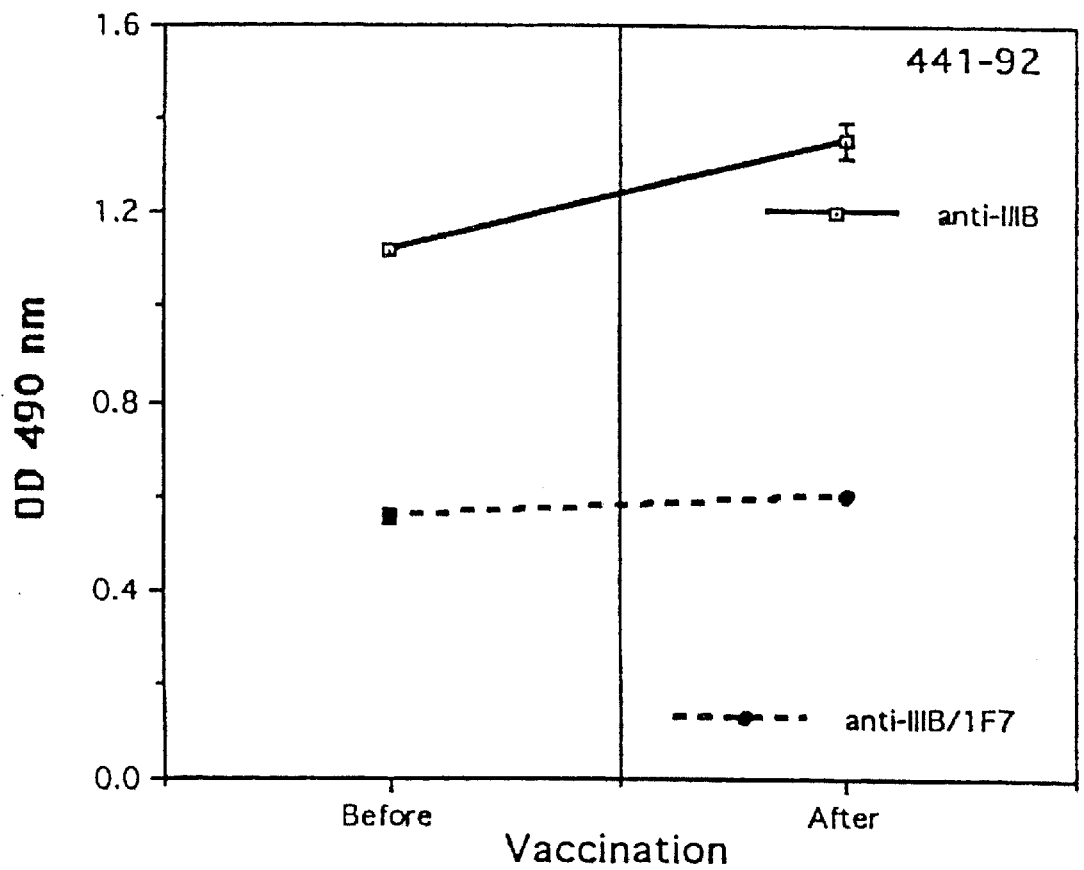
Figure 15A:
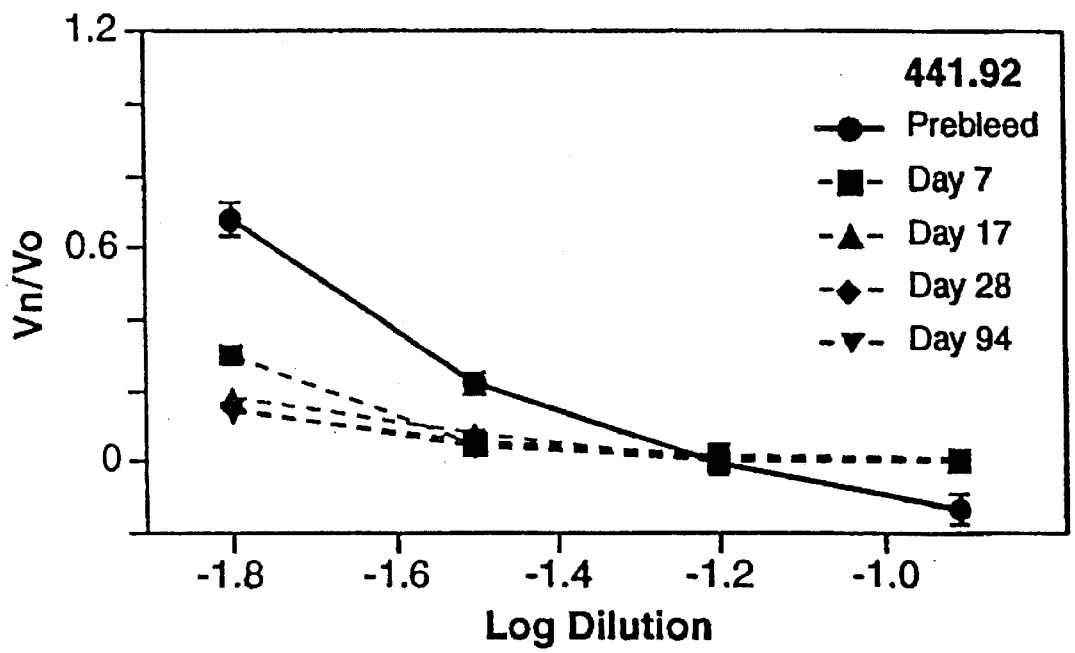

Monkey 441-92 was vaccinated six times with 5 mg each of mAb 1F7. Following 1F7 vaccination, monkey 441-92 showed increased virus neutralization of both IIIB (FIG. 14A) and MN (FIG. 15A) strains. With respect to virus IIIB, neutralization curves were significantly different from baseline (pre-bleed) on days 17 ($p=0.0012$), 35 ($p=0.0019$) and 94 ($p=0.0009$). With respect to virus MN, neutralization curves were significantly different from baseline on days 7 ($p=0.0044$), 17 ($p=0.016$), 28 ($p=0.015$), and 94 ($p=0.013$).

b) Monkeys 149-93 and 337-91

Figure 14B:
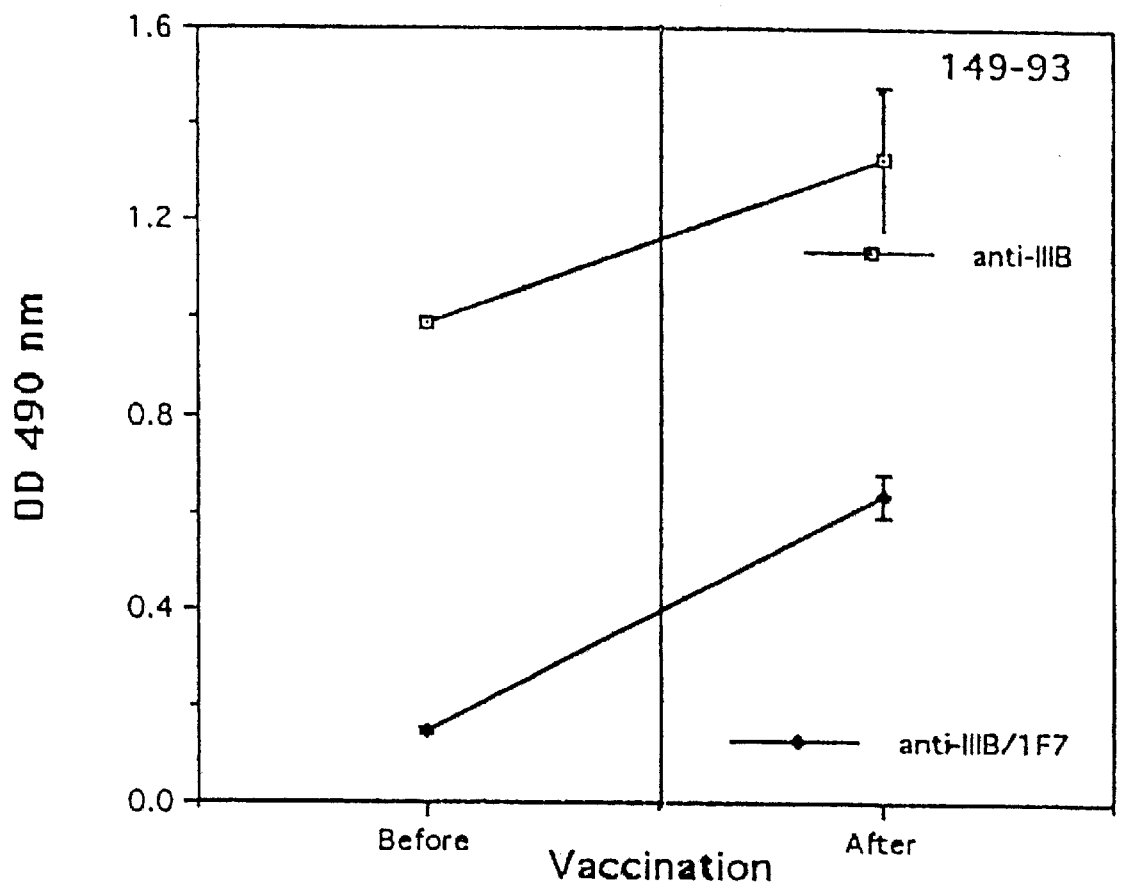
Figure 14C:
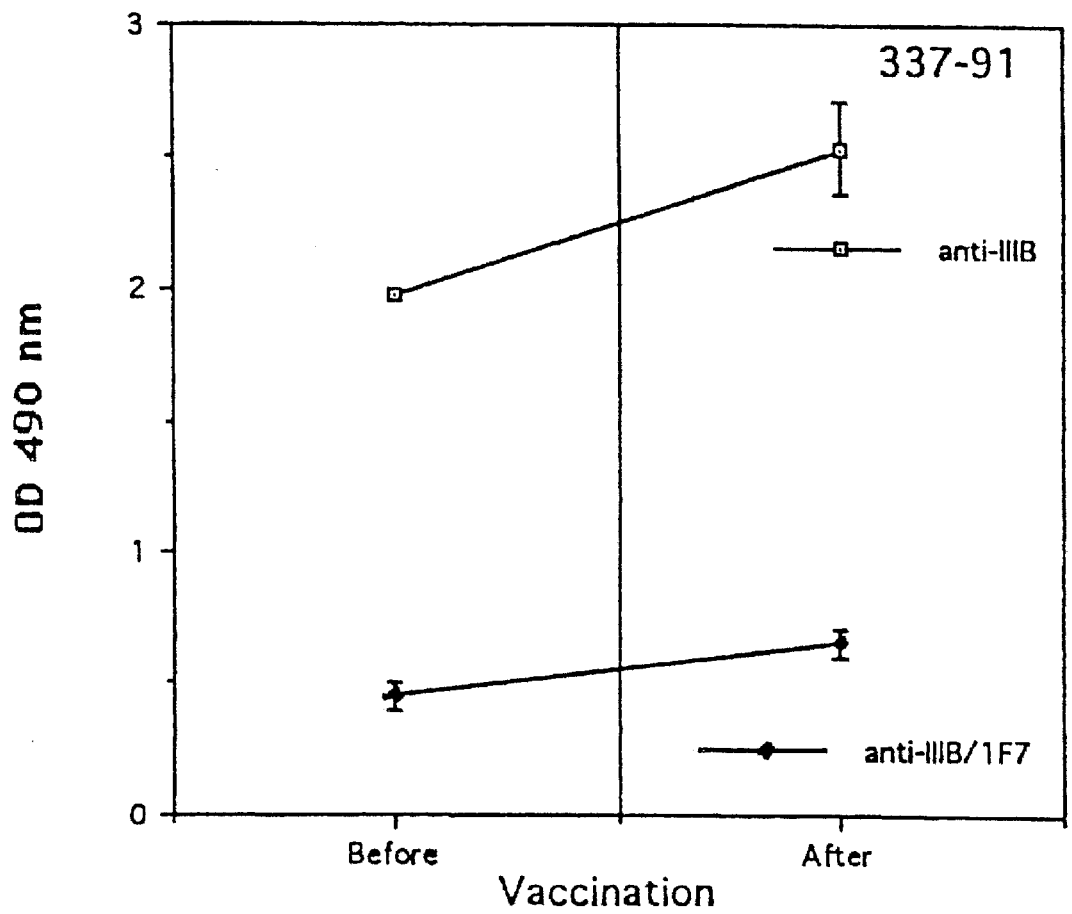
Figure 15B:
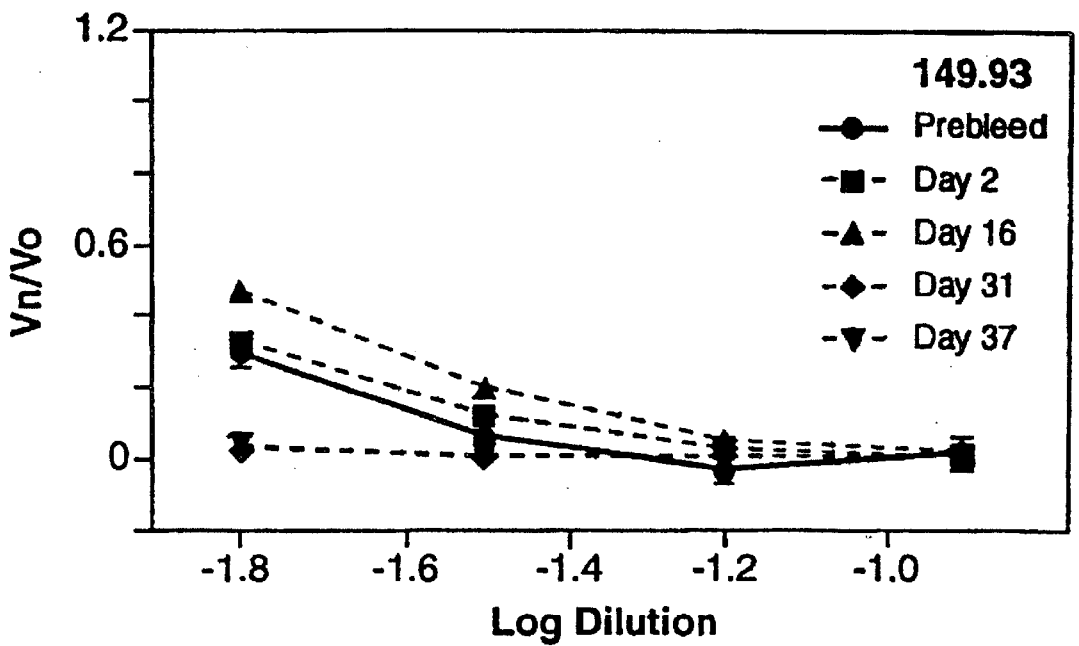
Figure 15C:
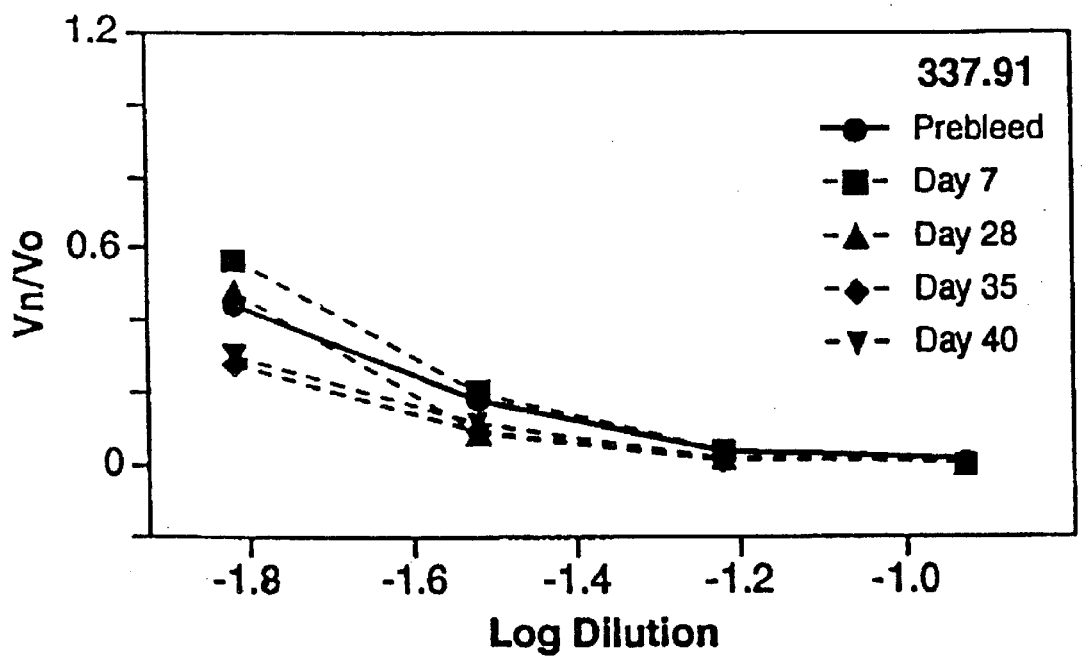

Monkeys 149-93 and 337-91 were both immunized four times with 5 mg mAb 1F7 antibody resulting in a total dose of 20 mg mAb 1F7 per macaque. Antibody neutralization activity for HIV-1 IIIB and MN increased significantly after four inoculations of 1F7 in monkey 149-93 as determined at day 31 ($p=0.028$, FIG. 14B) and 37 ($p=0.024$, FIG. 14B). A transient decrease, however, was detected prior to the increase at day 2 of IIIB virus neutralization (FIG. 14B). Enhanced antibody neutralization activity for HIV-1 MN almost achieved significance for day 31 ($p=0.062$, FIG. 15B) and day 37 ($p=0.066$, FIG. 15B). Monkey 337-91 showed no change in IIIB virus neutralization activity (FIG. 14C), but had significant increases in MN virus neutralization activity on days 35 ($p=0.0075$) and 40 ($p=0.0067$) (FIG. 15C).

c) Monkey 42-93 (Control)

Figure 14D:
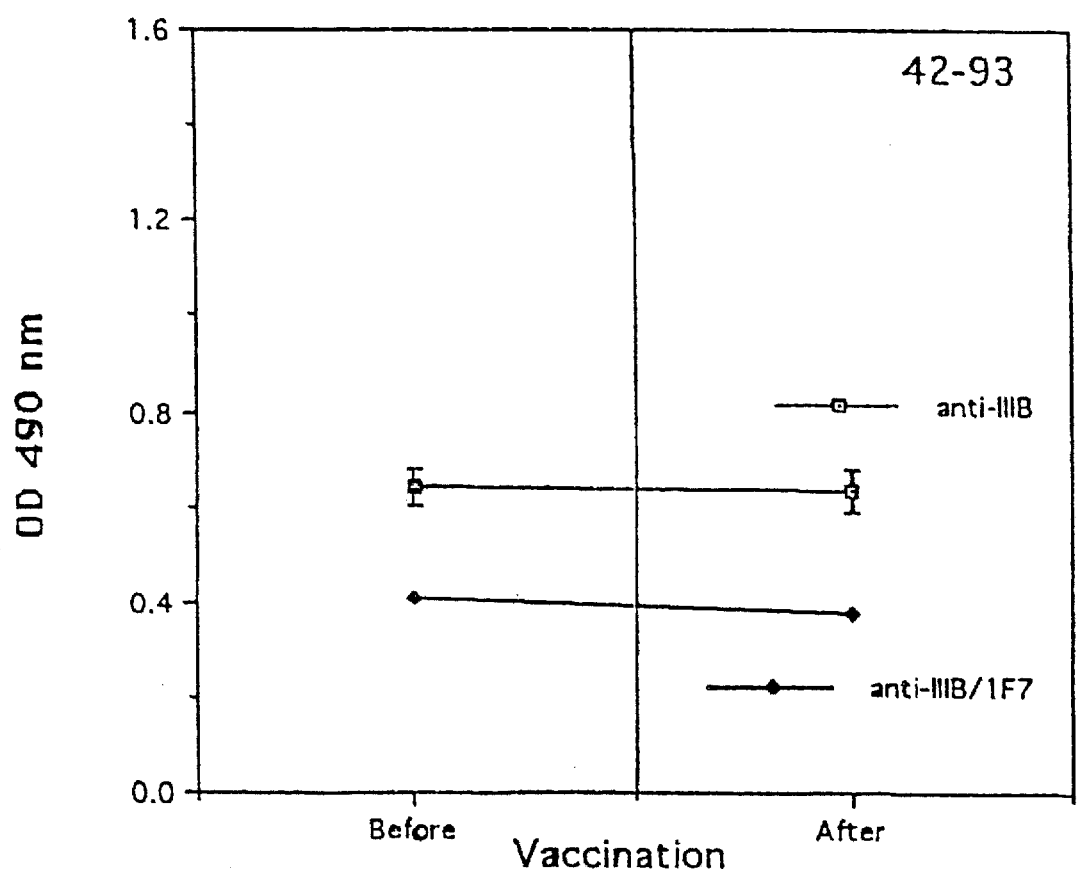
Figure 15D:
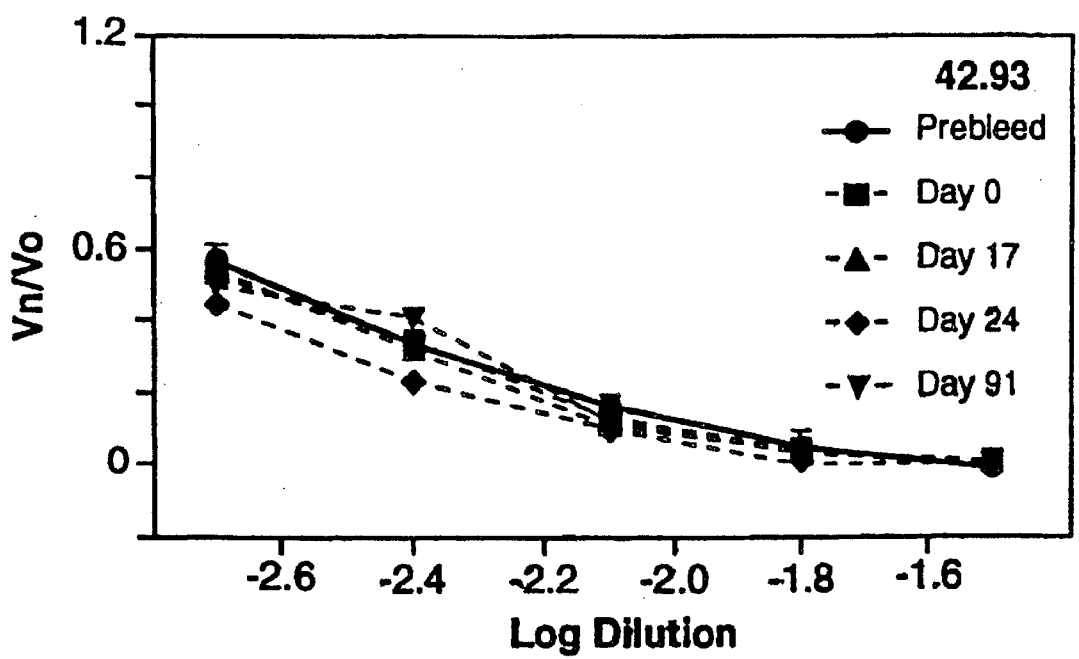

To determine whether HIV-1 neutralizing antibodies increased in response to clonotypic stimulation or in a non-specific reaction to murine monoclonal antibodies, one SHIVIIIB infected monkey was immunized with the mouse monoclonal mAb TEPC 183, an isotype matched for 1F7. Monkey 42-93 was immunized four times with 5 mg mAb antibody resulting in a total dose of 20 mg mAb TEPC 183. As shown in FIGS. 14D and 15D the IIIB and MN neutralizing antibodies did not change before, during or after the immunization with the isotype control antibody during up to three months of follow-up.

In conclusion, the relative changes with respect to the pre-vaccine neutralizing antibody titers for all four monkeys can be summarized as follows: In monkey 441-92 antibodies neutralizing IIIB and MN increased after 1F7 vaccination beginning at day 7 and remained higher compared to the pre-vaccine virus neutralizing antibody titer. Monkey 149-93 showed an initial decrease of neutralization potency at days 2 and 16 for IIIB and MN. The neutralization titer, however increased significantly over pre-vaccine levels by days 31 and 37. In monkey 337-91, no increase of IIIB neutralization was evident, while a statistically significant increase of antibodies neutralizing the non-homologous MN strain was observed. The control TEPC 183 monkey did not show significant changes in either IIIB or MN neutralization.

These data show that immunization with four and six, respectively, i.v. doses of 5 mg mAb 1F7 did induce significant changes, lasting up to three months, in the potency of endogenous antibodies mediating neutralization of HIV-1.

Discussion

Infection with human immunodeficiency virus (HIV) elicits strong immune responses by B-lymphocytes and T-lymphocytes which appear to be directed at non-protective, immunodominant epitopes and fail to eradicate viral infection. This occurs, in part, because the immune system is unable to control the virus variants which arise because of error-prone viral replication and selection pressures, including immunity. The humoral response to viral proteins in HIV-1 infected human and non-human primates is characterized by restriction of clonal heterogeneity which is stable in magnitude and antibody composition over time and characteristic for each patient, a sort of "immune fingerprinting" (97–99). Detection of oligoclonal spectrotypes, characterized by a few clusters of bands, of anti-gp120 and-p24 antibodies in sera and cerebrospinal fluid of HIV-1 infected patients has been interpreted as evidence that during infection a limited number of HIV epitope specific B cell clones are expanded. Similar stability of clonal composition was observed with T cells in HIV-1 infected patients (100). The restriction of the HIV specific antibody repertoire in HIV-1 and SIV infection is also apparent using the monoclonal anti-idiotypic antibody 1F7 (87). The 1F7 mAb recognizes antibodies reactive with several HIV-1 and SIV antigens in the majority of infected subjects (87,90,99). Thus, 1F7 functions as public idiotope marker in HIV-1 infection and provides an opportunity to manipulate the anti-viral response in infected individuals.

In HIV-1 infected individuals, circulating antibodies typically are inefficient in neutralizing the infecting virus. An increase in neutralizing immunity is one aim of both preventive vaccine and immune therapies of HIV-1 infection.

The concept of stimulating the immune response in infected patients is well established and such a therapeutic vaccine approach has been recently proposed for AIDS by Salk (101). The classical vaccine therapy approach relies on using virus-derived material, such as inactivated virus (101) to boost and broaden the anti-HIV-1 immune response in infected individuals. An alternative approach uses antibodies which either mimic HIV-1 epitopes or function as anti-clonotypic antibodies as immunogen. Our approach, described here, takes advantage of the oligoclonal nature of the antibody response in HIV-1 infection and the availability of an anti-idiotypic antibody (1F7) which reacts with antibodies against env and gag viral epitopes (90). mAb 1F7 presumably also reacts with the antigen receptors on B-cells capable of producing these antibodies. By analogy with anti-clonotypic antibodies against T-cell receptors, 1F7 may also be able to stimulate B-cells with the corresponding receptor idiotype. Because 1F7 is not an anti-idiotypic antibody which mimics antigen, the optimal administration is without adjuvant. Thus, using antibodies against public idiotopes becomes an alternative strategy to classical virus based formulations for developing therapeutic vaccines.

To test the effect of a clonotypic vaccine we have employed the SHIV-infected macaque model. This non-human primate model is well suited to evaluate immunostimulatory mechanisms because the chimeric virus expresses human viral envelope protein and induces a 1F7-reactive clonotypically restricted anti-viral response, similar to human HIV-1 infection (87,99). The pig-tail monkey infected with HIV-1 may be an alternative suitable model (102), however, it is not known whether their antibodies' response is 1F7 positive.

This study was conceived as an preclinical pilot trial using a non-human primate infection model which shares several immunological characteristics with the human HIV-1 infection, including the variability of the infection and its immune response. Four SHIV-infected macaques were selected which had anti-virus antibodies expressing the public 1F7 idiotype marker. Three monkeys were treated with 1F7, while one monkey was injected with an irrelevant isotype matched control antibody. Our primary outcome measure was the potency and strain specificity of virus neutralizing antibodies during up to three months follow up.

The effect of 1F7 injections on the neutralization profiles and potency of standardized HIV-1 laboratory strains was evaluated. The neutralization curves for all three animals receiving mAb 1F7 shared a significant shift at one or more time points for one or both viruses. Animals 441-92 and 149-93 demonstrated the greatest shifts in their curves for both HIV-1 IIIB and HIV-1 MN. The initial decrease of neutralization on days 2 and 16 in monkey 149-93 might be explained by transient suppression of antiviral antibodies by mAb 1F7 or by immune complex formation with the injected mAb.

It should be noted that the monkey with strongest increase of neutralizing antibodies (monkey 441-92) had received the largest vaccine dose. This suggests that vaccine dose escalation could enhance the therapeutic effects. The TEPC 183 isotype control antibody injected animal 42-93 demonstrated no shifts in the neutralization curves for either virus either before, during or after injections demonstrating the overall stability of the neutralization response both in vivo and in vitro over time. Significant shifts in the neutralization curves as compared to "pre-bleeds" occurred for all animals within 7 to 35 days following the first injection of 1F7. In two animals, 441-92 and 149-93 for both viruses a significant shift in the neutralization curves was noted out to 94 days.

An increase of antibodies against the envelope were also detected in solid phase binding assays. The changes in titer of anti-gp120 antibodies in 1F7 vaccinated macaques did not exactly parallel the observed changes in neutralizing activities, since it is known that not all envelope binding binding antibodies are also virus neutralizing. A detailed study of the anti-gp120 titer kinetic using strain different gp120 proteins (data not shown) revealed also boosting and broadening effects induced by 1F7 vaccination.

These results demonstrate that 1F7 is capable of modifying an existing virus neutralizing response and also of inducing operationally "de novo" neutralizing antibodies against the non-infecting MN virus. Regarding the underlying mechanisms two hypotheses will be tested in follow-up studies: (i) induction of neutralizing antibodies via direct clonotypic stimulation of 1F7 positive B-cells; (ii) suppression of dominant 1F7 positive B-cells allowing non-committed B-cells presursors to respond to escape virus epitopes.

The increases in potency and breadth of neutralizing activities may favorably impact the virus load and eventually also disease progression. In this study, using the non-pathogenic SHIV-IIIB virus, the virus load is below detectability with standard assays and therefore could not be monitored. In addition, the infected animals remain healthy for years and changes in disease progression were unlikely to occur during the time of observation. Having established that mAb 1F7 can increase and broaden the virus neutralization activity in chronically infected, healthy monkeys a follow-up study with animals infected with a more virulent strain is warranted prior to a trial with HIV-1 infected humans.

The examples presented hereinabove are provided for purposes of clarity and understanding. It will be apparent to those of skill in the art that various obvious modifications and variations may be practiced without departing from the spirit or scope of the invention. The pertinent disclosures of all patents and publications cited herein are incorporated by reference in their entireties.

REFERENCES

1. Fauer, A. S., R. L. Gallo, S. Koenig, S. Salk, and R. H. Purcell, 1989. Development and evaluation of a vaccine for human immunodeficiency virus (HIV) infection, *Ann. Intern. Med.* 110:37.
2. Jerne, N. K. 1974. Towards a network theory of the immune system, *Ann. Immunol. (Paris)* 125C.373.
3. McNamara, M., R. Ward, and H. Kohler. 1984. Monoclonal idiotype vaccine against *Streptococcus pneumoniae* infection. *Science* 226:1325.
4. Kohler, H., S. Muller, and C. Bona. 1985. Internal idiotype antigens. *Proc. Soc. Exp. Biol. Med.* 178:195.
5. Kohler, H., S.-V. Kaveri, T. Kieber-Emmons, W. J. W. Morrow, S. Muller, and S. Ravenaudhuri, 1989. Overview of idiotypic networks and the nature of molecular mimicry. *Methods Enzymol.* 178:3.
6. Chen, J. J., Y. Saeki, and H. Kohler. 1990. Idiotype matching: correlation of expression of idiotype in sera with survival of tumor mice. *J. Immunol.* 144:753.
7. Gaulton, G., and D. Wetner. 1990. Viral infections, in Idiotypic Network and Disease, J. Cerny and Hierneaux, eds. American Society for Microbiology, Washington, D.C. p. 523.
8. Uytdehaag, F. G. C. M., and A. D. M. E. Osterhaus. 1985. Induction of neutralizing antibody in mice against poliovirus type II with monoclonal anti-idiotypic antibodies. *J. Immunol.* 134:1225.
9. Fung, M. S. C. C. R. Y. Sun, R. S. Liou, W. Gordon, N. T. Chang, T-W. Chang, and N-C. Sun. 1990. Monoclonal anti-idiotypic antibody mimicking the principal neutralization site in HIV-1 gp120 induces HIV-1 neutralizing antibodies in rabbits. *J. Immunol.* 145:2199.
10. Shoenfeld, Y., D. A. Isenberg, J. Rauch, M. P. Madzio, B. D. Stoller, and R. S. Schwartz. 1983. Idiotypic cross-reactions of monoclonal human lupus autoantibodies. *J. Exp. Med.* 158:718.
11. Solomon, G., J. Schiffenbauer, H. D. Keiser, and B. Diamond. 1983. Use of monoclonal antibodies to identify shared idiotypes on human antibodies to native DNA from patients with systemic lupus erythematosus. *Proc. Natl. Acad. Sci. USA* 80:850.
12. Victor-Korbin, C., T. Manser, T. M. Moran, T. Imanishi-Karl, M. Gefter, and C. Bons. 1985. Shared idiotypes among antibodies encoded by heavy chain variable region (VH) gene members of the J558 VH family as basis for cross-reactive regulation of clones with different antigen specificity. *Proc. Natl. Acad. Sci. USA* 82:7696.
13. Goldberg, B., W. E. Paul, and C. Bona. 1983. Idiotype-anti-idiotype regulation. *J. Exp. Med.* 158:515.
14. Hahn, B. H., and F. M. Ebling. 1984. Suppression of murine lupus nephritis by administration of an anti-idiotypic antibody to anti-DNA. *J. Immunol.* 132:187.
15. Zanetti, M. 1985. Idiotypic regulation of autobody production. *CRC Crit. Rev. Immunol.* 6:151.
16. Devash, Y., T. Calvelli, D. G. Wood, K. J. Reagan, and A. Rubinstein. 1990. Vertical transmission of human immunodeficiency virus is correlated with the absence of high-affinity/avidity maternal antibodies to the gp120 principal neutralizing domain. *Proc. Natl. Acad. Sci. USA* 87:3445.
17. Robinson, E. W., D. C. Montefiori, W. M. Mitchell, A. M. Prince, H. J. Alter, G. R. Dreesman, and J. W. Eichberg. 1989. Antibody-dependent enhancement of human immunodeficiency virus type 1 (HIV-1) infection in vitro by serum from HI-1 infected and passively immunized chimpanzees. *Proc. Natl. Acad. Sci. USA* 86:47.
18. Ohlin, M., P-A. Broliden, L. Danielsson, M. Jondal, J. Rosen, B. Wahren, and A. K. Borrenbeck. 1989. Human monoclonal antibodies specific for cytomegalovirus or HIV-1 antigens. In *Abstract Book of Seventh International Congress of Immunology*, Berlin. Abstr. 98–91.
19. Prince, A. M., B. Horowitz, L. Baker, R. W. Shulman, H. Ralph, J. Volinsky, A. Cundell, B. Brotman, W. Boehle, F. Rey, M. Piet, H. Reesink, N. Lelie, M. Tersmette, F. Miedema, L. Barbosa, G. Nemo, C. L. Nastala, J. S. Allan, D. R. Lee, and J. W. Eichberg. 1988. Failure of a human immunodeficiency virus (HIV) immune globulin to protect chimpanzees against experimental challenge with HIV. *Proc. Natl. Acad. Sci. USA* 85:6944.
20. Kang, C-Y., and H. Kohler. 1986. Immunoglobin with complementary paratope and idiotope. *J. Exp. Med.* 163:787.
21. Kang, C-Y., P. Nara, S. Chamat, V. Caralli, T. Ryskamp, N. Haigwood, R. Newman, and H. Kohler. 1991. Evidence for non-V3 specific neutralizing antibodies in HIV-1 infected humans which interfere with gp120/CD4 binding. *Proc. Natl. Acad. Sci. USA*. In press.
22. Sultan, Y., F. Rossi, and M. D. Kazatchkine. 1987. Recovery from anti-VIII:C (anti-hemophilic factor) autoimmune disease is dependent on generation of anti-idiotypes against anti-VIII:c autoantibodies. *Proc. Natl. Acad. Sci. USA* 84:828.
23. Tankersley, D. L., M. S. Preston, and J. S. Finlayson. 1988. Immunoglobulin G dimer: an idiotype-anti-idiotype complex. *Mol. Immunol.* 25:41.
24. Fauci, A. S., R. C. Gallo, S. Koenig, J. Salk, and R. H. Purcell. 1989. Development and evaluation of a vaccine for human immunodeficiency virus (HIV) infection. *Ann. Int. Med.* 110:373.
25. Oi, V. T., and L. A. Herzenberg. 1980. In *Selected Methods in Cellular Immunology*. B. B. Mishell and S. M. Shisi, eds. W. H. Freeman and Co., San Francisco and London. p. 640.
26. Garmendia, A. E., M. V. Borca, D. O. Morgan, and B. Baxt. 1989. Analysis of foot and mouth disease virus-neutralizing idiotypes from immune bovine and swine with anti-murine idiotype antibody probes. *J. Immunol.* 143:3015.
27. Cormont, F., P. Manouvriez, L. de Clerco, and H. Bazin. 1986. In *Methods of Enzymology, Vol.* 121. J. J. Langone and H. Van Vanukis, eds. Academic Press. New York. p 622.
28. Cuatrecasas, P. 1970. Protein purification by affinity chromatography: derivation of agarose and polyacrylamide beads. *J. Biol. Chem.* 245:3059.
29. Towbin, H., T. Staehelin, and J. Gordon. 1979. Electrophoretic transfer of proteins from polyacrylamide gels to nitrocellulose sheets: procedure and some applications. *Proc. Natl. Acad. Sci. USA* 76:4350.
30. Engvall, L. E., and P. Perlman. 1972. Enzyme-linked immunoabsorbent ELISA III. Quantitation of specific antibodies by enzyme-labeled anti-immunoglobulin in antigen-coated tubes. *J. Immunol.* 109:129.
31. Bayer, E. A., and K. M. Wilchek. 1980. The use of avidin-biotin complex as a tool in molecular biology. *Methods Biochem. Anal.* 26:1.
32. Pahwa, G., M. T. J. Quilop, M. Lange, R. N. Pahwa, and M. H. Grieco. 1984. Defective B-lymphocyte function in homosexual men in relation to the acquired immunodeficiency syndrome. *Ann. Intern. Med.* 101:757.
33. Levine, A., B. E. Henderson, L. Groshen, K. Burnett, F. Jensen, R. Peters, D. Carlo, M. Gersten, and J. Salk. 1990. Immunization of HIV-infected individuals with inactivated HIV immunogen: significance of HIV-specific cell mediated immune response. Abstract in vol. 1:204. Sixth International Conference on AIDS. San Francisco, Calif. U.S.A., June 1990.
34. Halpern, R., S-V. Kaveri, and H. Kohler. 1991. Human anti-PC antibodies share idiotopes and are self-binding. *J. Clin. Invest.* In press.
35. Zhou, S-R., and J. N. Whitaker. 1990. An idiotype shared by monoclonal antibodies to different peptides of human myelin basic protein. *J. Immunol.* 145:2554.
36. Kohler, H. 1990. Idiotypic vaccines: role of network antigen. In *Immunotherapeutic Prospects of Infectious Diseases*. K. N. Masihi and W. Lange, eds. Springer-Verlag, Berlin and Heidelberg. p. 367.
37. Borrebaeck, C. A. U., L. Danielson, and S. A. Moller. 1988. Human monoclonal antibodies produced by primary in vitro immunization of peripheral blood lymphocytes. *Proc. Natl. Acad. Sci. USA* 85:3995.
38. Miller, R. A., S. Hart, M. Samoszuk, C. Coulter, S. Brown, D. Czerwinski, B. S. Kilenberg, L. Royston, and R. Levy. 1989. Shared idiotypes expressed by human B-cell lymphomas. *N. Engl. J. Med.* 321:851.
39. Livneh, A., A. Halpern, D. Perkins, A. Lazo, R. Halpern, and B. Diamond. 1987. A monoclonal antibody to a cross-reactive idiotype on cationic anti-DNA antibodies expressing lambda light chains: a new reagent to identify a potentially differential subset. *J. Immunol.* 138:123.
40. Davidson, A., A. Smith, H. Katz, J-L. Preude-Homme, A. Solomon, and B. Diamond. 1989. A cross-reactive idiotype in anti-DNA antibodies defines a H chain determinant present almost exclusively on IgG antibodies. *J. Immunol.* 143:179.
41. Isenberg, D. A., Y. Schoenfeld, M. P. Madaio, J. Rauch, M. Reichlin, M. B. D. Stollar, and R. S. Schwartz. 1984. Anti-DNA antibody idiotypes in systemic lupus erythematosus. *Lancet* 2:1417.
42. Kipps, T. J., E. Tomhave, P. P. Chen, and R. I. Fox. 1989. Molecular characterization of a major autoantibody-associated cross-reactive idiotype in Sjogren's syndrome. *J. Immunol.* 142:4261.
43. Lucas, A. H. 1988. Expression of crossreactive idiotypes by human antibodies specific for the capsular polysaccharide of *Hemophilus influenzae* B. *J. Clin. Invest.* 81:480.
44. Schreiber, J. R., M. Patawaran, M. Tosi, J. Lennon, and G. B. Pier. 1990. Anti-idiotype-induced, lipopolysaccharide-specific antibody response to *Pseudomonas aeruginosa*. *J. Immunol.* 144:1023.
45. Lee, W., H. Cosenza, and H. Kohler. 1974. Clonal restriction of the immune response phosphorytholine. *Nature* 247:55.
46. Zhou, E-M., K. L. Lohman, and R. C. Kennedy. 1990. Administration of non-internal image monoclonal anti-idiotypic antibodies induces idiotype-restricted responses specific for human immunodeficiency virus envelope glycoprotein epitopes. *Virology* 174:9.
47. Popovic, M., Sarngardharan, M. G., Reed, E. et al. (1984) *Science* 224,497.
48. Barre-Sinoussi, R., Chermann, J. C., Rey, E. et al. (1984) *Science* 220, 868–871.
49. Cohen, J. (1993) *Science* 262, 980–981.
50. Weiss, R. (1993) *Science* 260, 1273–1279.
51. Mendis, K. N., David, P. H. and Carter, R. (1991) *Immunol. Today* 12, 34–37.
52. Wang, S. Z., Rushlow, K. E., Issel, C. J. et al. (1994) *Virology* 199, 247–251.
53. Nara, P. L., Garrity, R. R. and Goudsmit, J. (1991) *FASEB J.* 5,2437–3455.
54. Nara, P. L., Smit, L., Dunlop, N. et al. (1990) *J. Virol.* 63, 3779–3791.
55. Kusumi, K., Conway, B., Cunningham, S. et al. (1992) *J. Virol.* 66, 875–885.
56. Kuiken, C. L., de Jong, J. J., Bean, E., Keulen, W., Tersmettle, M. and Gondsmit, J. et al. (1992) *J. Virol.* 66, 4622–4627.
57. Zwart, G., Langedijk, M., van der Hoek, L. et al. (1991) *Virology* 181, 481–489.
58. Pantaleo, G., Gaziesl, C. Demarest, J. R. et al. (1993) *Nature* 362, 355–358.
59. Grimaldi, L. M. E., Roos, R. P., Devare, S. G. et al. (1988) *J. Immunol.* 141, 114–117.
60. Amadore, A., Gallo, P., Zamarchi, R. et al. (1990) *AIDS Res. Hum. Retrovirus* 6, 581–586.
61. D'Amello, R., Biselli, R., Nisini, R. et al. (1992) *J. AIDS* 5, 930–935.
62. Muller, S., Nara, P., D'Amelio, R. et al. (1992) *Int. Rev. Immunol.* 9, 1–13.
63. Wolfe, T. F. W., Zwart, G., Bakker, M., Valk, M., Kuiken, C. L. and Gondsmit, J. (1991) *Virology* 185, 195–205.
64. Muller, S., Wang, H. T., Silverman, G., Bramlet, G. and Kohler, H. (1993) *Scand. J. Immunol.* 38, 327–334.
65. Saitta, M., Invarone, A., Cappela, N., et al. (1992) *Clin. Chem.* 38, 2454–2457.
66. Silverman, G. I., Carson, D. A., Solomon, A. et al. *Immunol. Methods* 95, 249–257.
67. Sasano, M., Bruton, D. R., and Silverman, G. J. (1993) *J. Immunol.* 151, 5822–5839.
68. Metlas, R., Veljkovic, V., Paladini, R. and Pongor, S. (1991) *Biochem. Biophys. Res. Commun.* 179, 1056–1062.
69. Veljkovic, V. and Metlas, R. (1992) *Immunol. Today* 13, 38.
70. Berberian, L., Goodglick, L., Kipps, T. J. and Braun, J. (1993) *Science* 261, 1588–1591.
71. Kang, C. T., Hariharan, K., Posner, M. R. and Nara, P. (1993) *J. Immunol.* 151, 449–458.
72. Livneh, A., Preud'Homme, J. L., Solomon, A. and Diamond, B. (1987) *J. Immunol.* 139, 3730–3733.
73. Rowley, D. and Stach, R. (1993) *J. Exp. Med.* 178, 835–851.
74. Stach, R. M. and Rowley, D. A. (1993) *J. Exp. Med.* 178, 841–852.
75. Clerici, M., Sison, A. V., Berzofsky, J. A. et al. (1993) *AIDS* 7,1427–1433.
76. Kanagawa, O., Vaupel, B. A., Gayama, S., Koehler, G. and Kopf, M. (1993) *Science* 262, 240–242.
77. Salk, J., Brescher, P. A., Salk, P. L., Clerici, M. and Shearer, G. M. (1993) *Science* 260, 1270–1272.
78. Kohler, H., Goudsmit, J., and Nara, P. (1992) *J. AIDS* 5, 1158–1168.
79. Nara, P. L., Robey, W. G., Pyle, S. W. et al. (1988) *J. Virol.* 62, 2622–2628.
80. Garrity, R. R., Lin, G., Dunlop, N. and Nara, P. (1994) *Vaccines* 94 (Brown, F., Chanok, R., Ginsberg, H. and Norby, E., eds., pp. 261–267, Cold Spring Harbor Laboratory Press.
81. Cozena, H. and Kohler, H. (1972) *Proc. Natl. Acad. Sci. USA* 69, 2701–2705.
82. Hart, D. A., Wang, A. L., Pawlak, L. L. and Nisonoff, A. (1972) *J. Exp. Med.* 135, 1293–1300.

83. Wang., H., Muller, S., Zolla-Pazner, S., and Kohler, H. (1992) *Eur. J. Immunol.* 22, 1749–1755.
84. Muller et al., *The Journal of Immunology,* Aug. 1, 1991, "Generation and specificity of monoclonal anti-idiotypic antibodies against human HIV specific antibodies".
85. Reimann, K. A., et al., (1997) *J. Virol.* 70, 3198–3205.
86. Newman, R., et al., (1992) *Biotechnology* 10, 1455–1460.
87. Müller, S., et al., (1997) *Hybridoma,* 16, 17–21.
88. Guide for the Care and Use of Laboratory animals. Department for Health and Human Serviced Publication No. (NIH) (1985) 85-23. National Institute of Health, Bethesda, Md.
89. Müller S., et al., (1991) *J. Immunol.* 147, 933–941.
90. Wang H. T., et al. (1992) *Eur J. Immunol.* 22, 1749–1755.
91. Tsuji, K., et al., (1980) *Appl. Environ. Microbiol.* 40, 533–538.
92. Nara, P. L., et al., (1987) *AIDS Research and Human Retroviruses* 3, 283–302.
93. Kang, C. Y., et al. (1992) *Proc. Natl. Acad. Sci. USA* 89, 2546.
94. Draper, Nr. et al. (1981) Applied Regression Analysis (Second Edition), Wiley, New York.
95. Milliken, G. A., et al., (1978) *Comm. Statist. Theory and Models* 7, 65–69.
96. Alvord, W. G., et al. (1990), *Mutation Research,* 240, 171–194.
97. Müller S., et al. (1993) *Scand. J. Immunol.* 38, 327–334.
98. D'Amelio R., et al. (1992) *J. AIDS* 5, 930–935.
99. Grant, M. D., et al. (1996) *Immunol. Cell. Biol.* 74, 38–44.
100. Levraud, J.-P., et al. (1997) *J. Immunol.* 158, 3335–3343.
101. Salk J. (1987) *Nature.* 327, 473–476.
102. Frumkin L R; et al. *Virology.* (1993) 195, 422–31.

What is claimed is:

1. An isolated polypeptide wherein the amino acid sequence of said polypeptide is selected from the group consisting of SEQ ID NO:5, SEQ ID NO:6, SEQ ID NO:7, SEQ ID NO:8, SEQ ID NO:9, and SEQ ID NO:10.

2. The polypeptide of claim 1, which is conjugated to a label.

3. The polypeptide of claim 2, wherein the label is a chromophore, fluorophore, chemiluminescent material or radioisotope.

4. A composition comprising at least one polypeptide of claim 1 and a physiologically acceptable carrier.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 37 nucleotides
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

ACTAGTCGAC ATGAAATGCA GCTGGGTCAT STTCTTC          37

(2) INFORMATION FOR SEQ ID NO:2:

(i) SEQUENCE CHARACTERISTICS:
      (A) LENGTH: 32 nucleotides
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CCCAAGCTTA CGAGGGGGAA GACATTTGGG AA          32

(2) INFORMATION FOR SEQ ID NO:3:

(i) SEQUENCE CHARACTERISTICS:
      (A) LENGTH: 33 nucleotides
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GGGAATTCAT GGAGACAGAC ACACTCCTGC TAT                                  33

(2) INFORMATION FOR SEQ ID NO:4:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

CCCAAGCTTA CTGGATGGTG GGAAGATGGA                                      30

(2) INFORMATION FOR SEQ ID NO:5:

(i) SEQUENCE CHARACTERISTICS:
            (A) LENGTH: 41 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

Asp Ile Val Leu Thr Asn Ser Pro Ala Ser Leu Ala Val Ser Leu Gly
    1               5                  10                  15

Gln Arg Ala Thr Ile Ser Cys Lys Ala Ser Gln Ser Val Asp Tyr Asp
                    20                  25                  30

Gly Asp Ser Tyr Met Trp Tyr Gln Gln
                    35                  40

(2) INFORMATION FOR SEQ ID NO:6:

(i) SEQUENCE CHARACTERISTICS:
            (A) LENGTH: 41 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

Lys Pro Gly Gln Pro Pro Lys Leu Leu Thr Ile Ala Ala Ser Asn Leu
    1               5                  10                  15

Glu Ser Gly Ile Pro Ala Arg Phe Ser Gly Ser Gly Ser Gly Thr Asp
                    20                  25                  30

Phe Thr Leu Asn Ile His Pro Val Glu
                    35                  40

(2) INFORMATION FOR SEQ ID NO:7:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

```
Glu Glu Asp Ala Ala Thr Tyr Tyr Cys Gln Leu Cys Asn Glu Asp Pro
 1               5                  10                  15

Pro Thr Phe Gly Ala Gly Thr Lys Gln Gln Gln Lys
            20                  25
```

(2) INFORMATION FOR SEQ ID NO:8:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:8:

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
            20                  25                  30

Phe Met Gly Val Ser Trp Ile Arg Gln
            35                  40
```

(2) INFORMATION FOR SEQ ID NO:9:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:9:

```
Pro Ser Gly Lys Gly Leu Glu Trp Leu Ala His Ile Tyr Trp Asp Asp
 1               5                  10                  15

Asp Lys Arg Tyr Asn Pro Ser Leu Lys Ser Arg Leu Thr Ile Ser Lys
            20                  25                  30

Asp Thr Ser Ser Asn Gln Asp Phe Leu
            35                  40
```

(2) INFORMATION FOR SEQ ID NO:10:

```
    (i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

Lys Ile Thr Ser Val Asp Thr Arg Asp Thr Ala Thr Tyr Tyr Cys Ala
  1               5                  10                  15

Arg Arg Val Ser Leu Thr Ala Tyr Ala Met Asp Tyr Trp Gly Gln Gly
                  20                  25                  30

Thr Ser Val Thr Val Ser Ser
              35
```